United States Patent [19]
Shimazu et al.

[11] Patent Number: 5,961,467
[45] Date of Patent: *Oct. 5, 1999

[54] CARDIOVASCULAR SYSTEM OBSERVATION METHOD

[76] Inventors: Hideaki Shimazu, 14-11, Gotokuji 1-chome, Setagaya-Ku, Tokyo 154; Masaru Komatsu, 4880-7, Osachi, Okaya-shi, Nagano 394, both of Japan

[*] Notice: This patent is subject to a terminal disclaimer.

[21] Appl. No.: 08/829,852

[22] Filed: Apr. 1, 1997

Related U.S. Application Data

[63] Continuation-in-part of application No. 08/347,428, filed as application No. PCT/JP94/00545, Apr. 1, 1994, Pat. No. 5,680,867.

[30] Foreign Application Priority Data

Apr. 2, 1993 [JP] Japan ................................ 5-100444

[51] Int. Cl.⁶ ............................................. A61B 5/00
[52] U.S. Cl. .................... 600/485; 600/494; 600/495; 600/500
[58] Field of Search ...................... 600/485, 450, 600/493–496, 504, 500, 526

[56] References Cited

U.S. PATENT DOCUMENTS

| | | |
|---|---|---|
| 3,126,885 | 3/1964 | Hinman . |
| 3,903,872 | 9/1975 | Link . |
| 3,908,639 | 9/1975 | McIntyre . |
| 4,178,918 | 12/1979 | Cornwell . |
| 4,312,359 | 1/1982 | Olson . |
| 4,337,778 | 7/1982 | Akira et al. . |
| 4,343,314 | 8/1982 | Sramek . |
| 4,349,034 | 9/1982 | Ramsey, III . |
| 4,432,373 | 2/1984 | Ogawa et al. . |
| 4,484,584 | 11/1984 | Uemura . |
| 4,517,986 | 5/1985 | Bilgutay . |
| 4,570,225 | 2/1986 | Lundy . |
| 4,592,364 | 6/1986 | Pinto . |
| 4,625,277 | 11/1986 | Pearce et al. . |
| 4,649,929 | 3/1987 | Weaver et al. . |
| 4,651,747 | 3/1987 | Link . |
| 4,690,151 | 9/1987 | Utsunomiya et al. . |
| 4,703,760 | 11/1987 | Miyawaki et al. . |
| 4,735,213 | 4/1988 | Shirasaki . |
| 4,754,406 | 6/1988 | Miyawaki et al. . |
| 4,754,761 | 7/1988 | Ramsey, III et al. . |
| 4,771,790 | 9/1988 | Yamasawa et al. . |
| 4,776,344 | 10/1988 | Shirasaki et al. . |
| 4,819,654 | 4/1989 | Weaver et al. . |
| 4,821,735 | 4/1989 | Goor et al. . |
| 4,830,019 | 5/1989 | Shirasaki et al. . |
| 4,844,084 | 7/1989 | Yamasawa . |
| 4,850,368 | 7/1989 | Miyawaki . |
| 4,860,760 | 8/1989 | Miyawaki et al. . |
| 4,860,761 | 8/1989 | Yamasawa et al. . |
| 4,862,895 | 9/1989 | Yamasawa et al. . |
| 4,870,973 | 10/1989 | Ueno . |
| 4,873,967 | 10/1989 | Sutherland . |
| 4,880,013 | 11/1989 | Chio . |
| 4,922,918 | 5/1990 | Ruiter . |

(List continued on next page.)

FOREIGN PATENT DOCUMENTS

| | | |
|---|---|---|
| 0 197 302 A2 | 10/1986 | European Pat. Off. . |
| 0 483 355 A1 | 5/1990 | European Pat. Off. . |

*Primary Examiner*—Robert L. Nasser
*Attorney, Agent, or Firm*—Dorn, McEachran, Jambor & Keating

[57] ABSTRACT

A cardiovascular system observation method using a computer processor on the basis of pulse wave amplitude data obtained from a patient in a compressed state which changes, said method comprising: process steps for forming measurement patterns expressing the transition of pulse wave amplitude values by smoothing minute fluctuations of said pulse wave amplitude data and normalizing the pulse wave amplitude values and pulse wave intervals of said pulse wave amplitude data; process steps for extracting the features of the measurement patterns; and process steps for judging the pattern shape to judge reference pattern groups to which said measurement pattern belongs by using said features.

18 Claims, 39 Drawing Sheets

U.S. PATENT DOCUMENTS

| | | |
|---|---|---|
| 4,993,420 | 2/1991 | Welkowitz et al. . |
| 5,092,343 | 3/1992 | Spitzer et al. . |
| 5,094,244 | 3/1992 | Callahan et al. . |
| 5,094,245 | 3/1992 | Shirasaki . |
| 5,101,828 | 4/1992 | Welkowitz et al. . |
| 5,103,831 | 4/1992 | Niwa . |
| 5,156,158 | 10/1992 | Shirasaki . |
| 5,161,538 | 11/1992 | Fukura et al. . |
| 5,178,152 | 1/1993 | Ozawa . |
| 5,193,548 | 3/1993 | Miyawaki . |
| 5,211,177 | 5/1993 | Chesney et al. . |
| 5,218,966 | 6/1993 | Yamasawa . |
| 5,218,968 | 6/1993 | Apple . |
| 5,241,966 | 9/1993 | Finkelstein et al. . |
| 5,255,686 | 10/1993 | Takeda et al. . |
| 5,279,303 | 1/1994 | Kawamura et al. . |
| 5,303,711 | 4/1994 | Sciarra . |
| 5,316,004 | 5/1994 | Chesney et al. . |
| 5,316,006 | 5/1994 | Inage et al. . |
| 5,323,782 | 6/1994 | Shirasaki et al. . |
| 5,339,818 | 8/1994 | Baker et al. . |
| 5,349,519 | 9/1994 | Kaestle . |
| 5,381,797 | 1/1995 | Pak et al. . |
| 5,390,679 | 2/1995 | Martin . |
| 5,406,952 | 4/1995 | Barnes et al. . |
| 5,511,551 | 4/1996 | Sano et al. . |
| 5,518,000 | 5/1996 | Booth et al. . |
| 5,522,395 | 6/1996 | Shirasaki et al. . |
| 5,533,511 | 7/1996 | Kaspari et al. . |
| 5,551,440 | 9/1996 | Miyawaki . |
| 5,564,426 | 10/1996 | Iwai . |
| 5,570,694 | 11/1996 | Rometsch . |
| 5,579,776 | 12/1996 | Medero . |
| 5,579,778 | 12/1996 | Baker et al. ............................ 600/526 |
| 5,582,197 | 12/1996 | Dobberstein . |
| 5,584,299 | 12/1996 | Sakai et al. . |
| 5,651,370 | 7/1997 | Hersh et al. ............................ 600/494 |
| 5,730,138 | 3/1998 | Wang ...................... 600/503 |

FIG. 7
| TYPE | PATTERN | PULSE WAVE AMPLITUDE | TYPICAL CONDITION |
|---|---|---|---|
| A | 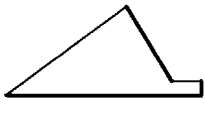 |  | Normal state |
| B |  |  | Hypotension, Anemia, Shock |
| C | 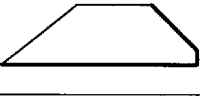 |  | Arteriosclerosis, Diabetes, Obesity, Old age, Intense Stress |
| D | 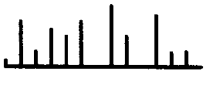 | 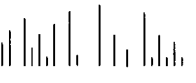 | Arrhythmia |
| E | 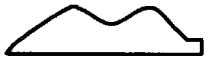 |  | Other Cardiac Conditions |

CARDIOVASCULAR SYSTEM OBSERVATION METHOD

CROSS-REFERENCES TO RERATED APPLICATIONS

This is a continuation-in-part application of the patent application, Ser. No. 08/347,428, now U.S. Pat. No. 5,680,867 filed on the basis of the international patent application, PCT/JP94/00545, filed on Apr. 1, 1994.

TECHNICAL FIELD OF THE INVENTION

The present invention relates to a cardiovascular system observation method, and in particular relates to a method and apparatus, which are constructed so as to observe the cardiovascular conditions showing the dynamic properties of blood vessels and cardiac output properties on the basis of pulse wave amplitude data of a patient.

BACKGROUND OF THE INVENTION

Conventionally, as non-invasion type blood circulation measuring equipment, various kinds of blood pressure measuring apparatuses constructed so that Korotkoff's sounds and fluctuations of pulse wave pressure, which are generated by changing the cuff pressure, are detected in a state that a cuff is wound on an arm of a patient and is inflated by supplying air, etc. so as to tighten the arm with pressure applied to surface of the body of a patient have been used. In these blood pressure measuring apparatuses, there are many cases where they display the systolic blood pressure, mean blood pressure, diastolic blood pressure, and pulse rate of a patient, and they are used to presume the blood circulation of the patient with these values.

In a method for measuring the blood pressure value on the basis of Korotkoff's sounds detected by a cuff, since the Korotkoff's sounds are small and simultaneously the frequency band of the corresponding Korotkoff's sounds is in such a range where Korotkoff's sounds are liable to be influenced by environmental noise, an erroneous detection is apt to occur, and since the attenuation amounts of the sound waves are greatly different, depending upon a detection part and/or the thickness of the upper part tissue, there occurs such a problem where the detection error becomes large and the repeatability thereof is bad.

Therefore, recently, an oscillometric method in which the blood pressure is directly detected from changes of a cuff pressure has been utilized. According to this method, pulse waves of a patient which are overlapped on the cuff pressure are extracted from detection signals obtained by a detection means such as a pressure sensor, etc., the pulse wave amplitude values are read, and the blood pressure value is determined by reference to the cuff pressure value obtained by the maximum value of the pulse wave amplitudes. In this case, the cuff pressure value at the point when the pulse wave amplitude shows the maximum value is displayed as a mean blood pressure value, the cuff pressure value at the point when the pulse wave amplitude multiplied by an appointed ratio for the corresponding maximum value is obtained at a higher pressure side of the cuff pressure than the maximum value is displayed as the systolic blood pressure value, and the cuff pressure value at the point when the amplitude value multiplied by an appointed ratio for the corresponding maximum value is obtained at a lower pressure side of the cuff pressure than the maximum value is displayed as the diastolic blood pressure.

In a blood pressure measurement by this oscillometric method, it is possible to utilize a high sensitivity pressure sensor, and a highly accurate and highly repeatability measurement, which is hardly influenced by environmental noise and environmental vibrations, is enabled since the detection signals thereof are in a low frequency band zone.

In almost all conventional blood pressure measuring apparatuses, only the systolic blood pressure value, mean blood pressure value, diastolic blood pressure value, and pulse rate are detected. Although these blood pressure values are influenced by the cardiac output conditions and conditions of arteriosclerosis, they are determined by various factors in a living body. Therefore, it is impossible to accurately grasp the cardiovascular conditions of a patient by merely checking the blood pressure values. Furthermore, it is impossible to correctly evaluate the meaning of the blood pressure values themselves unless there is some information other than the blood pressure values regarding the cardiovascular system of a patient. Therefore, it is impossible to make a correct diagnosis on the basis of only the blood pressure values obtained by any conventional sphygmomanometer, whereby it is real that the blood pressure values are regarded as mere references for medical diagnoses.

In the product process of a measuring apparatus in which an oscillometric method is used, the blood pressure values secured by a direct method in which a catheter is inserted into a blood vessel are compared in advance with the blood pressure values obtained by the measuring apparatus itself, calculation parameters of blood pressure values in the measuring apparatus are determined so that the blood pressure values obtained by the apparatus show the values identical to those secured by the direct method, and the measurement values secured by the measuring apparatus become as accurate as possible. However, various situations are considered in the cardiovascular system of a patient even in cases where the blood pressure values show almost the same values as those secured by the direct method. Still furthermore, even though a measurement apparatus is adjusted to be strictly accurate, there are cases where the blood pressure values secured by the measurement apparatus are greatly different from those secured by the direct method in some conditions of the cardiovascular system.

SUMMARY OF THE INVENTION

According to the invention, measurement patterns of pulse wave amplitude responsive to the cardiovascular condition of a patient can be obtained, which are not numerals such as blood pressure values, by a sphygmomanometer in which a conventional oscillometric method is used, on the basis of the detected pulse wave amplitude data (this includes pulse wave amplitude values of pulse wave signals obtained from a patient and generation time information of the pulse wave signals, for example, pulse wave intervals). The measurement pattern shows the cardiovascular conditions of a patient with the entire shape thereof.

The measurement pattern of pulse wave amplitudes substantially may express the transition of pulse wave amplitude values in the course during which the pressure applied to the surface of the body of a patient is being changed, and can be formed from pulse wave amplitude data through appointed numerical processes. These numerical processes may be include processes for eliminating noise and smoothing the fluctuations of pulse wave amplitude values in order to extract information brought by the cardiovascular system of a patient from the pulse wave amplitude data. Furthermore, there may be a case where the same includes a process for obtaining a pattern-shaped envelope by securing a curve adaptable to the pulse wave amplitude data.

Next, the features (the characteristic points) of the entire shape may be extracted from the shape of a measurement pattern in view of the cardiovascular system. Especially, the features regarding the peak shape of the measurement pattern can be extracted in view of the dynamic properties of blood vessels and the cardiac output properties of a patient, and simultaneously, timing irregularities of pulse wave generation can be calculated from the data of pulse wave generation intervals obtained from a patient. It is possible that the timing irregularities of pulse wave generation are obtained from a measurement pattern and are also obtained directly from the pulse wave amplitude data.

Furthermore, by comparing the features regarding the shape of said measurement pattern with a plurality of parameters pertaining to a plurality of reference pattern groups, that is, a plurality of reference values established in advance from the features of the pattern shape of a plurality of reference pattern groups, the measurement pattern can be caused to correspond to one or more reference pattern groups of said plurality of reference pattern groups, corresponding to the situations of the cardiovascular system of a patient.

Furthermore, according to the invention, the computer program (software) operated by a computer can achieve and ensure that measurement patterns are formed on the basis of pulse wave data, the features of measurement patterns are extracted on the basis of measurement patterns or pulse wave amplitude data, and a judgement or classification of to which one or more reference pattern groups the measurement pattern belongs is made on the basis of the features thereof. The computer program may be constructed so that they can be run by a conventional personal computer system and may ensure that input operations necessary for operation and display output for displaying the results of measurement and processes are performed.

Still furthermore, the pulse wave amplitude data can be displayed in real time during the measurement. And after the measurement is finished, one or more blood pressure values and the results of judgement showing to which one or more reference pattern groups the measurement pattern belongs can be displayed. Still furthermore, the results of measurement and judgement previously recorded per patient can be called, listed and displayed.

According to the invention, the cardiovascular conditions of a patient can be given meanings in compliance with a plurality of classification standards. Furthermore, since an abnormalities regarding the cardiovascular system may be find out without any professional knowledge in the medical field, it is possible for a patient to consult a medical doctor before a serious symptom occurs and to receive adequate therapy or a suitable cure.

Furthermore, it is an object of the invention to provide a method by which since it is possible to store the corresponding results of measurement as patterns and to control measurement information without any missing thereof, consequently a specified patient is able to be observed from time to time with respect to the time-elapsing change of his medical condition, and statistical processes can be carried out for a plurality of patients.

Still furthermore, it is another object of the invention to provide a method which is able to propose clinical information pertaining to the cardiovascular system important to a person having professional knowledge in the medical field, for example, a medical doctor, and to clarify the reliability of blood pressure values which may be calculated simultaneously and physiological meanings to a medical doctor.

BRIEF DESCRIPTION OF THE DRAWINGS

FIG. 7 is a table showing the correlation between the typical examples (reference pattern groups) of measurement patterns of pulse wave amplitudes and the symptoms of a patient.

DETAILED DESCRIPTION OF THE INVENTION

A cardiovascular system observation method according to the invention is usually on the assumption that the pulse wave amplitude data is led out by a part of the oscillometric method, and is to propose information pertaining to the cardiovascular system of a patient on the basis of the pulse wave amplitude data. Furthermore, the method according to the invention ensures that, as a preferred embodiment thereof, the blood pressure values similar to those measured by a usual sphygmomanometer are displayed together with information regarding the blood circulation of a patient.

Before explaining the observation method of blood circulation, a description will be given of the relationship between the observation method of cardiovascular condition and the cardiovascular system of a living body. In a case where pulse waves are detected from a patient, in order to detect the blood pressure change corresponding to the beat of the heart of a patient, it is necessary to apply pressure to the surface of the body of a patient and to provide a pulse wave detecting means to detect the pressure fluctuations in response to the pulse waves. This pulse wave detecting means is required to have, in a usual living body non-invasion type sphygmomanometer, a cuff attached to the surface of the body of a patient, a pressure supplying device, for example, an air pump, control valves, etc., to apply an appointed pressure to the cuff, and a pressure sensor to detect the cuff pressure. Although the cuff is a very popular member in the field of blood pressure measurement, anything which is able to apply controlled pressure to the surface of the body of a patient may be acceptable.

The observation method according to the invention is based on the assumption that pulse waves are able to be detected in the course during which the pressure applied to the surface of the body of a patient is gradually increased or decreased, that is, in the course of low speed increase or low speed decrease of the cuff pressure. This method is identical to that used in the blood pressure measurement method which detects pressure by the oscillometric method. Therefore, it is possible to display the blood pressure values secured by a usual oscillometric method in addition to the observation of the blood circulation according to the invention. Both the observation method according to the invention and the conventional blood pressure measurement method basically utilize that the pulse wave constituents generated on the basis of the beat of the heart of a patient are overlapped onto the pressure applied to the surface of the body of a patient.

Figure 5:
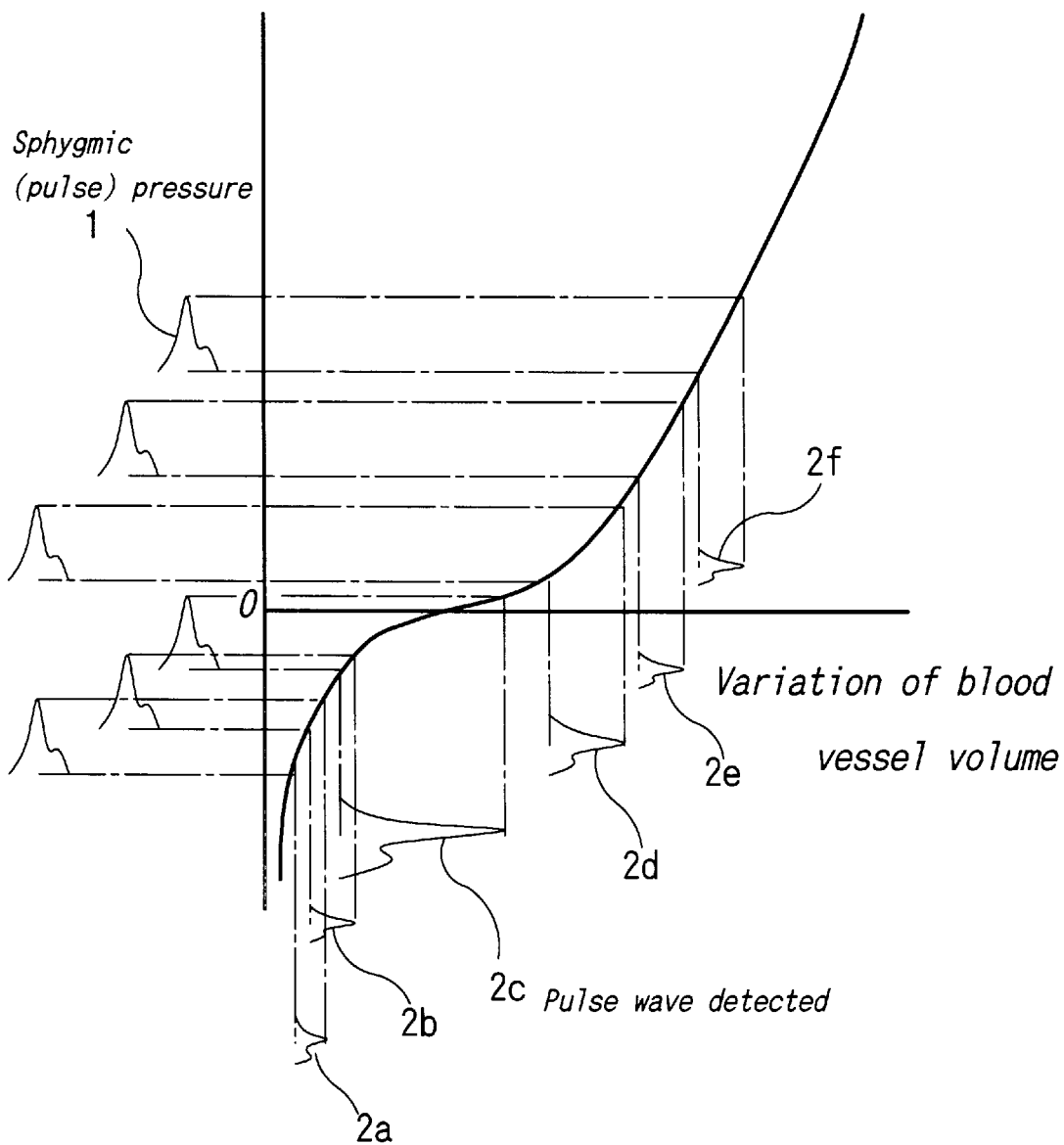
FIG. 5 is a graph showing the relationship between the difference between the internal pressure and the outer pressure of blood vessel and the volume(capacity) change of a blood vessel of a man of sound health.

The amplitude of pulse wave constituents overlapped onto the pressure applied to the surface of the body of a patient is determined by the difference between the internal pressure and outer pressure of blood vessel and the change quantity of the volume of the blood vessel resulting from the difference therebetween. FIG. 5 shows a graph the ordinate of which shows the difference between the internal pressure and outer pressure of blood vessel (that is the difference between the pressure inside a blood vessel and that outside the blood vessel of a patient), which is changed by applying pressure to the surface of the body of a patient, and the abscissa of which shows the change quantity of the volume of the blood vessel which changes, resulting from the fluctuations of the difference between the inner pressure and outer pressure. This graph and other similar graphs described later show the results obtained through experiments carried out with respect to the carotid artery of a patient. The inventor made clear that there exist non-linearity and hysteresis between the difference between the inner pressure and outer pressure and the change quantity of blood vessel capacity. As shown in FIG. 5, the change of the blood vessel capacity is made radically large when the difference between the inner pressure and outer pressure of a blood vessel is small. This shows that the blood vessel has a remarkably large expandability in a state where a pressure almost equal to the blood pressure (inner pressure) is applied from the outside thereof.

Figure 6A:
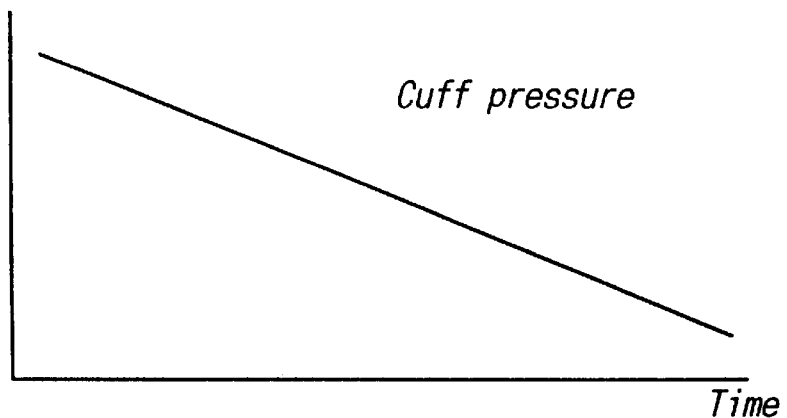
FIG. 6 is a graph showing the cuff pressure change (a) and pulse wave amplitude change (b) of a man of sound health.
Figure 6B:
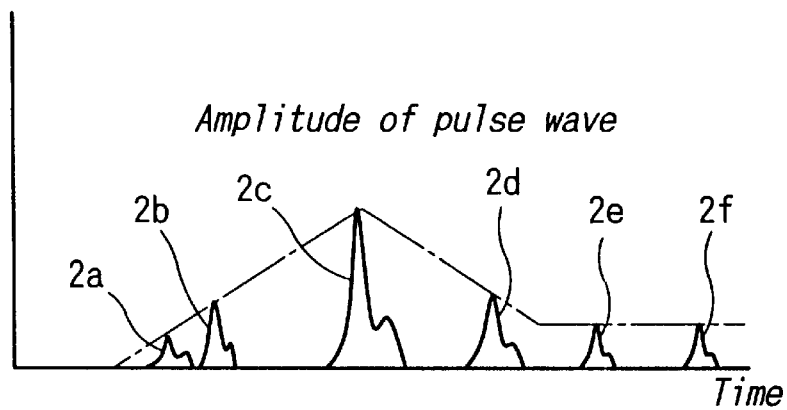

Such expandability of a blood vessel as shown in FIG. 5 changes the amplitude of the detected pulse wave which is obtained by the sphygmic(pulse) pressure 1 transmitted into a blood vessel by a heart beat in the course during which the pressure applied to the surface of the body of patient from the outside by a cuff, etc. is gradually changed. The range of the cuff pressure change is from a higher pressure than the mean blood pressure of a patient to a lower pressure than the mean blood pressure, and especially in order to obtain a complete measurement pattern, it is preferable that the range is from a pressure higher than the systolic blood pressure of a patient to a pressure lower than the diastolic blood pressure. As shown in FIG. 5 and FIG. 6, although the blood circulation itself stops when the cuff pressure is very high, small pulse waves 2a, 2b begin to be detected from a certain point by gradually decreasing the cuff pressure, and the pulse wave amplitudes gradually become large. At the point when the cuff pressure is made coincident with the mean pressure in a blood vessel, the amplitude of the pulse wave 2c shows the maximum value. By further decreasing the cuff pressure, the amplitudes of the pulse waves 2d, 2e, 2f are decreased, and they will be stabilized to be roughly at a constant pulse wave amplitude.

As described above, the non-linear properties with respect to the expandability of a blood vessel, that is, the changing properties of the elasticity of blood vessel result from the construction of blood vessel and the deformation properties of each element of the construction thereof. A blood vessel consists of elastic fibers composed of muscular tissue existing inside thereof and gelatiginous fibers having a low expandability, which surround the outside of the elastic fibers. In a case where a large external pressure is given to a blood vessel, although the blood vessel deformation due to the corresponding external pressure is suppressed, the blood vessel will have a large expandability since the tension of the blood vessel inner wall is retained mainly by elastic fibers when the difference between the inner pressure and outer pressure is decreased in line with a decrease of said external pressure. However, in a case where the external pressure is further decreased to cause the blood vessel to be expanded by the inner pressure, the blood vessel deformation is suppressed by gelatiginous fibers having less elasticity, thereby indicating a small expandability.

Generally, it is recognized that the blood pressure is reflected by the results brought by the functional states of the cardiovascular system. The functions of this cardiovascular system are determined by the strength of the beat of the heart, the other movements thereof and the total states of the blood vessel system. Since the pulse pressure generated by the beat of the heart is caused to reach the abovementioned measurement portion, for example, an arm through blood vessels, the pulse waves are detected through the surface of the body at the appointed portion in a form that the dynamic states of the blood vessel through which the pulse waves are transmitted are reflected in.

As described above, the amplitude of the pulse waves detected by the oscillometric method shows characteristic pattern shapes(envelopes) along with the changes of the cuff pressure. Although each of the blood pressure values of the systolic blood pressure, mean blood pressure and diastolic blood pressure is calculated from these pattern shapes, these pattern shapes includes much important information in addition to the blood pressure values. Although the blood pressure values merely indicate specified values of the pressure in a blood vessel, the pattern shape consisting of envelopes formed, for example, by the fluctuations of pulse wave amplitudes shown in FIG. 6 (b), which shows fluctuations of the typical pulse wave amplitude, includes much information showing the states of the cardiovascular system in the fluctuation of the pattern, for example, dynamic information of the cardiovascular system such as the pulsation quantity (stroke volume), pulsation strength of the heart, and flexibility of blood vessels. Furthermore, the same includes information which brings clues of morbid abnormality and/ or changes of the cardiovascular system.

The pulse wave amplitude values generally become large in cases where the expandability of blood vessels is large (the flexibility thereof is high) and the pulsation quantity (stroke volume) of the heart is large. Furthermore, the pattern shapes of the pulse wave amplitudes becomes much different from those of a man of sound health when a change occurs in the operating state of the beat of the heart and in the dynamic state of blood vessels, for example, when any abnormality occurs in the pulsations of the heart or the elastic fibers of blood vessels are hardened due to a certain reason.

FIG. 7 shows five basic typical pattern shapes regarding the pulse wave amplitude, that is, the reference pattern groups obtained by classifying the characteristic pattern shapes per medical symptom of a patient, which causes dynamic changes in the cardiovascular system. The pattern shapes belonging to these five reference pattern groups correspond to the medical states of a typical patient.

The reference pattern group A shows a pattern shape for the cardiovascular system, which is obtained from a man of sound health, and the same shows a single peak mountain shaped pattern. In this pattern shape, a pulse wave begins appearing from the point when the cuff pressure becomes almost the systolic blood pressure value, and the pulse wave amplitude is increased in line with a decrease of the cuff pressure. Meanwhile, after the same reaches the peak thereof, the pulse wave amplitude is decreased and almost no decrease occurs in the pulse wave amplitude when the cuff pressure comes near the diastolic blood pressure value. With the oscillometric method, in many cases, the value of the cuff pressure corresponding to the peak position of the pulse wave amplitude is regarded as the mean blood pressure value, the cuff pressure value at the high pressure side at which the pulse wave amplitude showing an appointed ratio for the peak position (maximum value) of the pulse wave amplitude is obtained is regarded as the systolic blood pressure value, and the cuff pressure value at the low pressure side at which the pulse wave amplitude showing an appointed ratio for the peak position (maximum value) of the pulse wave amplitude is obtained is regarded as the diastolic blood pressure value.

The reference pattern group B shows the pattern shapes obtained from a patient who is in a state of hypotension, anemia and shock. Even though the properties of a blood vessel itself is normal at the patient, the volume(capacity) change of the blood vessel is made small due to a low pressure in the blood vessel, and the pattern shape obtained from him shows a kind of flattened mountain pattern.

The pattern shape of the reference pattern group C is characteristic in a case where a patient is in a state of arteriosclerosis or intense stress. Concretely, the pattern shape is obtained from a patient who is in a state of arteriosclerosis, diabetes, obesity, oldage, and intense stress. The pattern shape is found in a case where the elasticity of blood vessel is lost, and the same is like a mountain having a flattened peak area.

The reference pattern group D shows a pattern shape obtained from a patient who is in a state of arrhythmia. Arrhythmia is such that the beat of the heart is irregularly lost, whereby the pulse wave amplitude data itself is irregularly missed.

The reference pattern group E is a pattern shape of a patient who suffers from other cardiac conditions, for example, who suffers from a latent or chronic failure. In many cases, this pattern shape shows that there is an abnormality in the pulsation of the heart, whereby the same pattern is of double-peak mountain shape or S-shaped curve.

Figure 8:
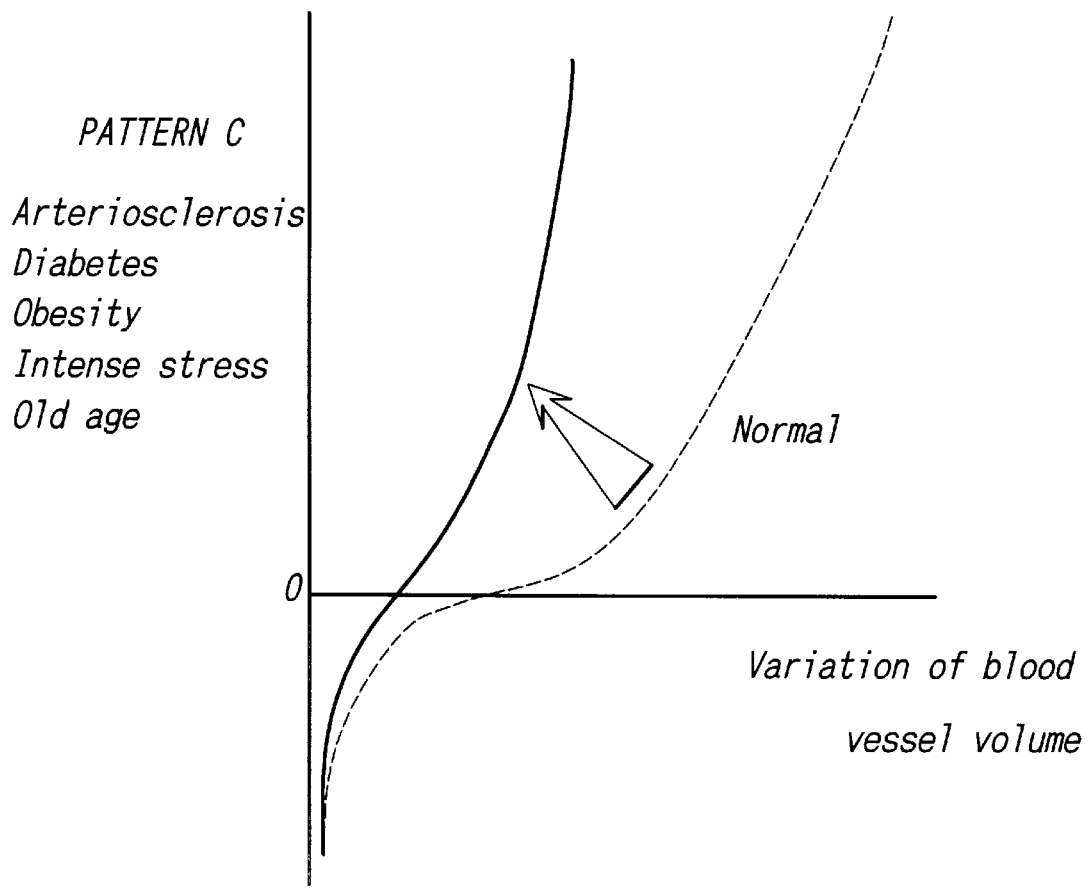
FIG. 8 is a graph showing the relationship between the difference between the inner pressure and outer pressure of blood vessel and the volume change of the blood vessel for a patient of whom the measurement pattern belonging to the reference pattern group C is detected.

FIG. 8 is a graph showing a comparison of the expandability of a blood vessel of a patient showing a pattern shape of the pulse wave amplitude belonging to the reference pattern group C with that of a blood vessel of a man of sound health, whose property is shown in FIG. 5. Although a sound blood vessel shows a large expandability in a state where there is no difference between the inner pressure and outer pressure of the blood vessel, the inclination of a curve showing the expandability in an area having less difference between the inner pressure and outer pressure become large since the flexibility of the elastic fibers is lost when arteriosclerosis occurs due to a certain cause. Thus, if the elasticity of blood vessels is increased due to arteriosclerosis or stress, generally it is considered that the value itself of the pulse wave amplitude is decreased. However, an increase of the elasticity of blood vessel accompanies an increase of resistance of the blood vessel, and since the blood pressure is increased and the pulsation becomes large due to an increase of this blood vessel resistance, the value of the pulse wave amplitude is not necessarily decreased.

Figure 9:
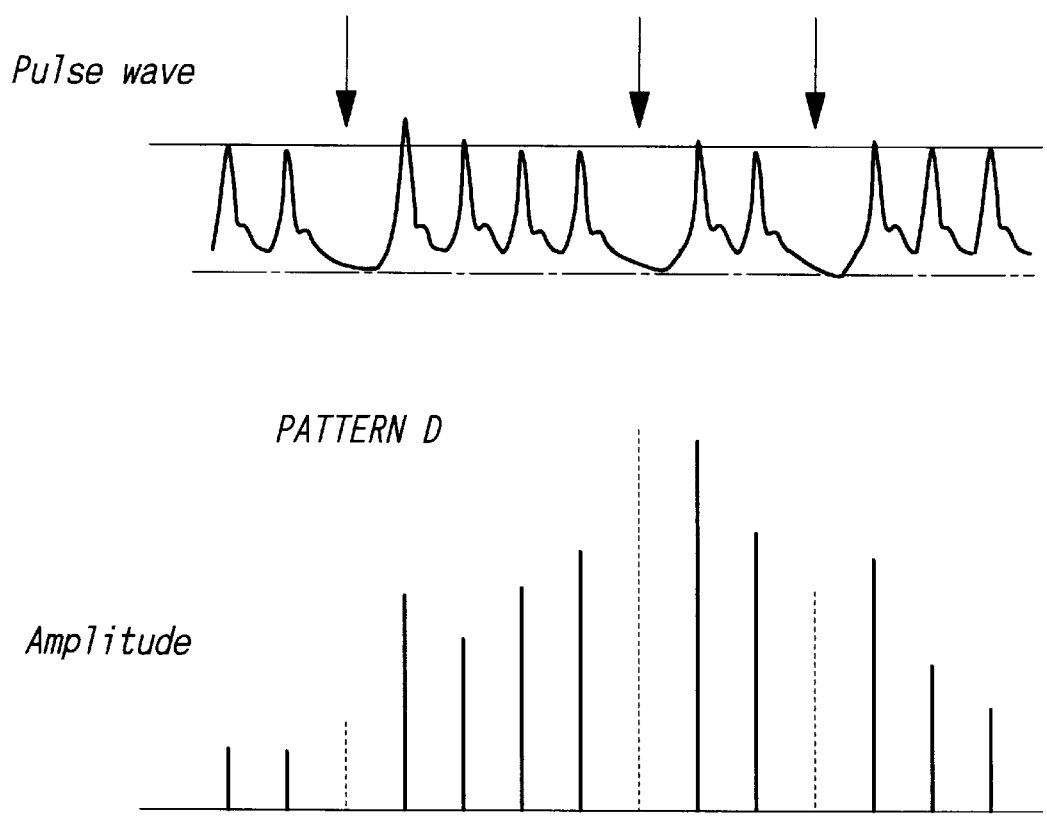
FIG. 9 is graphs showing the correlation between the pulse wave forms and the pulse wave amplitude change in a patient of whom the measurement pattern belonging to the reference pattern group D is detected.

In a case where a patient is in a state of arrhythmia, the capacity changes of the blood vessel does not become constant at every beat of the heart. In such a state, the shapes of pulse waves detected in the course during which the cuff pressure is decreased are made irregular, and the pulse wave intervals also become irregular. FIG. 9 shows the wave form of pulsation of a patient showing a symptom of arrhythmia and the values of the pulse wave amplitude corresponding thereto. In many cases of arrhythmia, the pulse wave amplitude thereof is observed in a state where a part of the beats which are periodically generated is missed. As a general tendency of arrhythmia, it is characteristic that, after a long-term slackening (diastolic state) of the heart, a large pulsation occurs since the cadiac output is increased due to a large stroke volume, and after a short-term slackening (diastolic state) of the heart, a small pulsation occurs since the pulsation quantity of the heart is decreased. If the cuff pressure is applied to the surface of the body of a patient who generates such pulse waves, irregular (choppy) pattern shape which is different from the pattern of an ideal pulse wave amplitude is shown as illustrated in FIG. 9.

Figure 10:
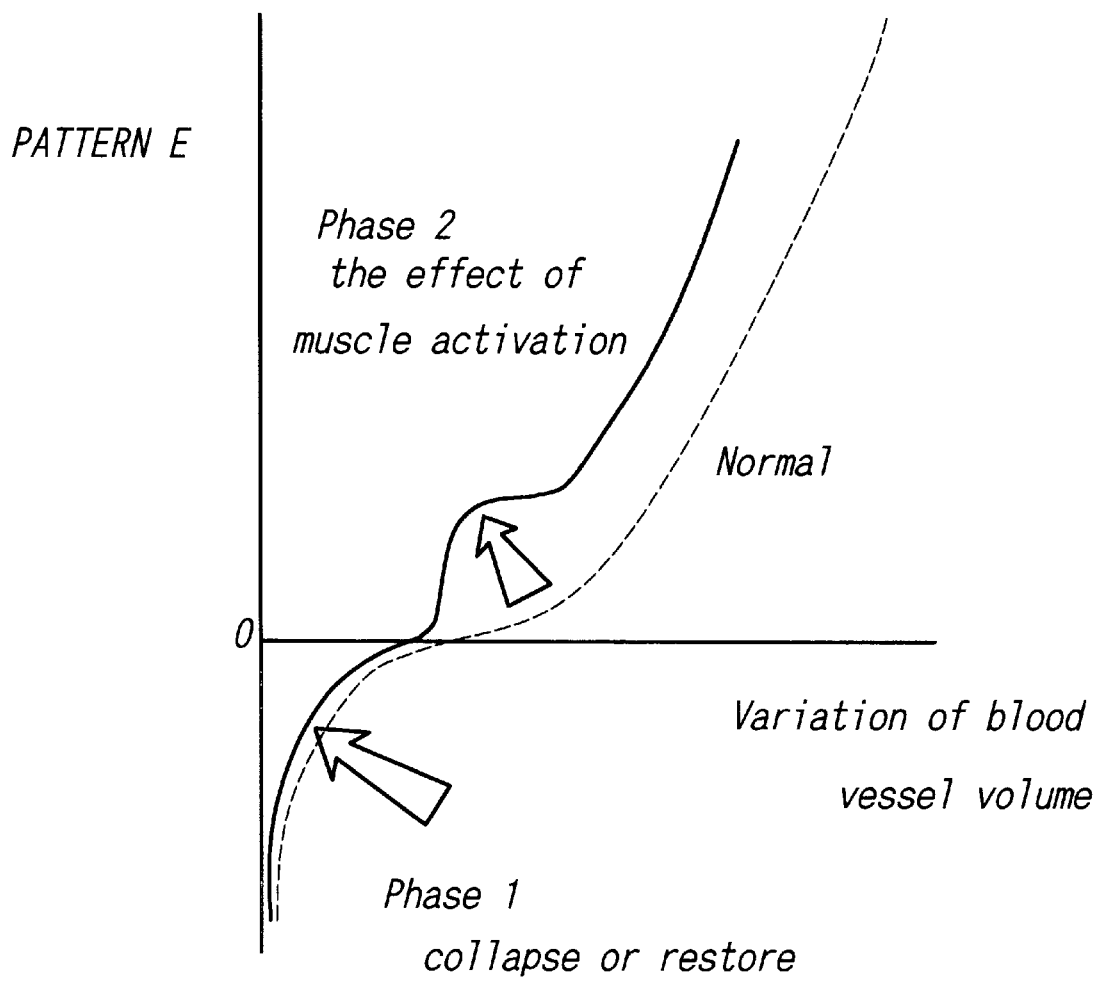
FIG. 10 is a graph showing the relationship between the difference between the inner pressure and outer pressure of blood vessel and the volume change of the blood vessel for a patient of whom the measurement pattern belonging to the reference pattern group E is detected.

In a case of a patient having a kind of heart disease, for example, chronic cardiac failure, it has been reported that muscular tissue of blood pressure is activated by larger stimulus, resulting from that a long-term intense stress is consecutively applied to peripheral blood vessels. In this case, as shown in FIG. 10, blood vessels are likely to be collapsed due to application of pressure from the outside, and at the same time even though the inner pressure is slightly higher than the outer pressure in an area where the difference between the inner pressure and outer pressure is small, the initial expansion of the blood pressure is difficult due to an effect of activation of the muscular tissue of blood vessel, and the expansion of blood vessel may occur after the inner pressure is increased to some degree. Thus, with a patient having such a state in the cardiovascular system, the pattern shape of the abovementioned reference pattern group E is obtained. However, there are still many points which are not clear, with respect to the relationship between such abnormalities in the arterial system and heart diseases and the relationship between these and pattern shapes corresponding thereto.

(System configuration)

Figure 3:
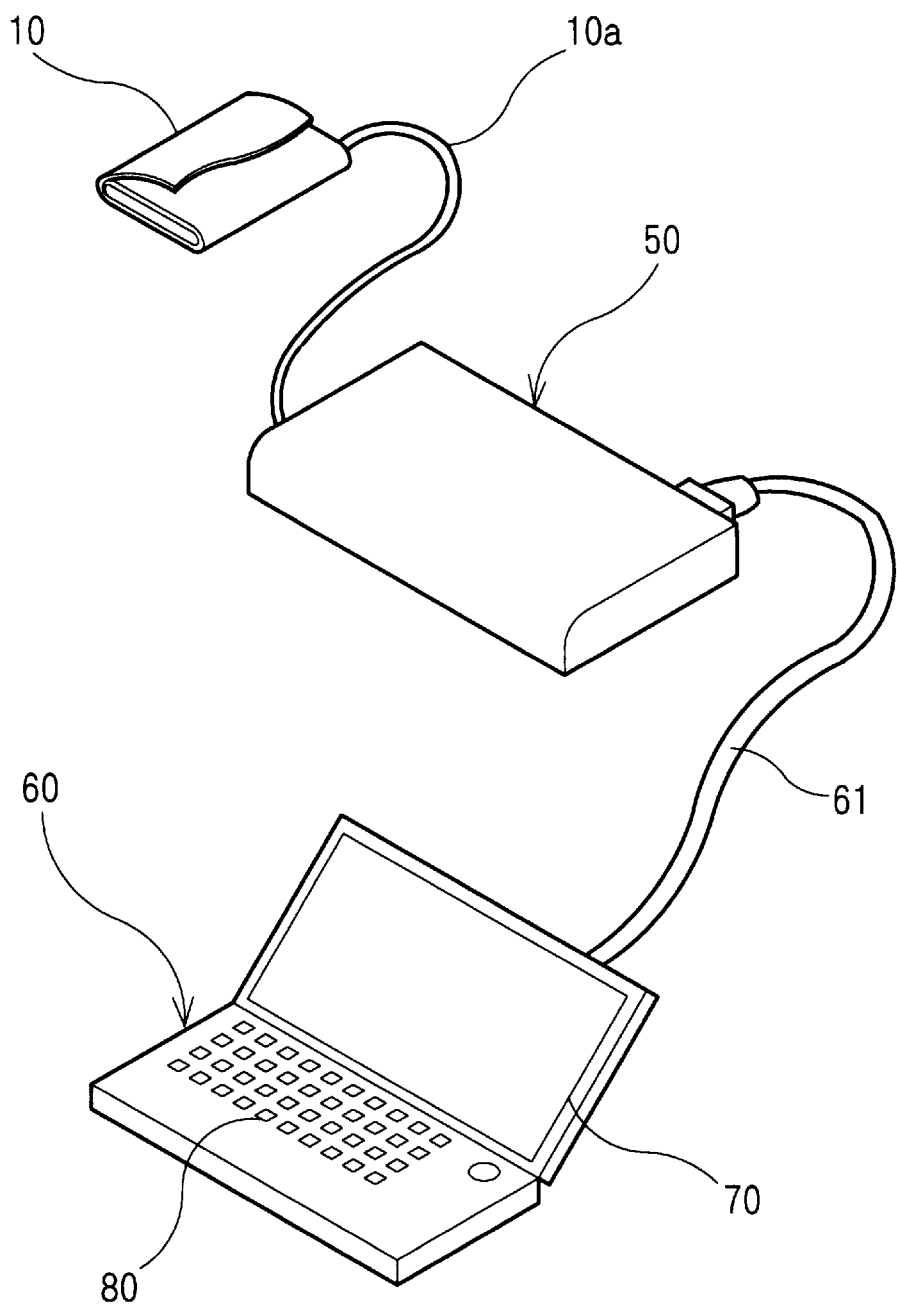
FIG. 3 is a perspective view showing a blood pressure measurement adaptor and a personal computer which are used in the preferred embodiment of the invention.
Figure 4A:
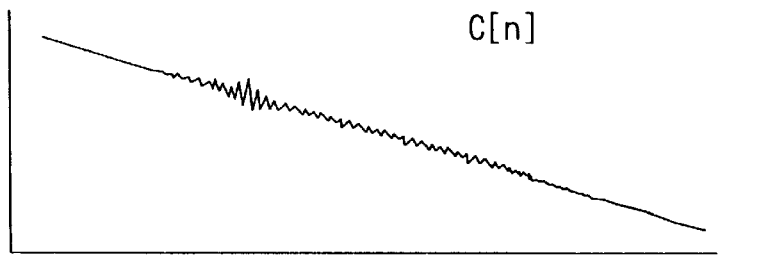
FIG. 4 is views respectively showing data wave forms (a) to (f) which show the data processing course in the preferred embodiment of the invention.
Figure 4B:
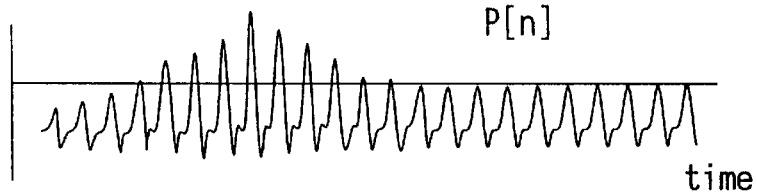
Figure 4C:
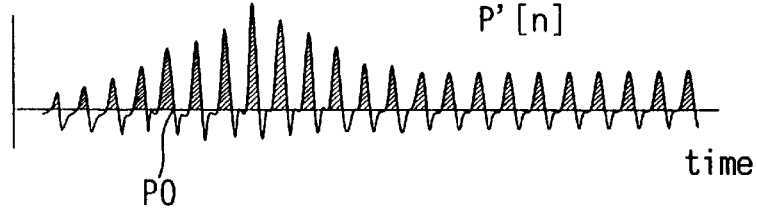
Figure 4D:
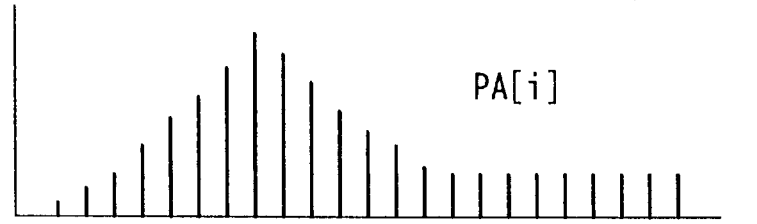
Figure 4E:
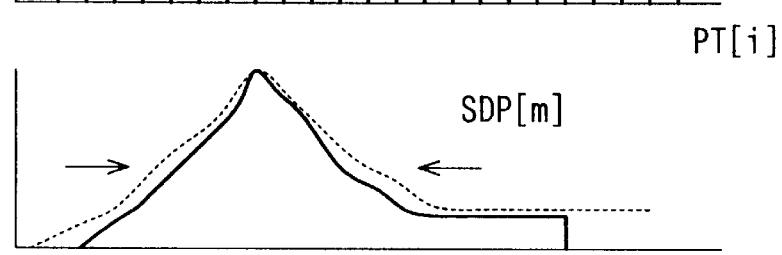
Figure 4F:
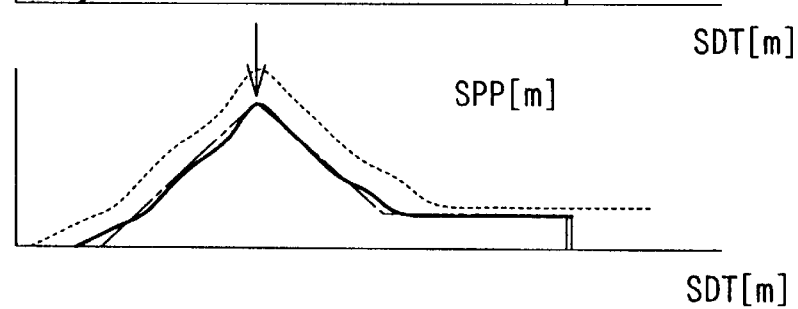

In a case where a detailed observation apparatus is constructed in order to achieve a method according to the present invention, for example, as shown in FIG. 3, said observation apparatus is composed of a cuff 10, a blood pressure measuring adaptor 50 connected to said cuff 10 by an air tube 1a, and a personal computer 60 connected to said blood pressure adaptor 50 via a connection cable 61 consisting of an RS232C interface cable, etc. A personal computer in which an operating system (OS) such as MS-DOS (Trademark), Windows 3.1X (Trademark) or Windows 95 (Trademark), etc. is incorporated in hardware compatible with an IBM (Trademark) machine may be used as the personal computer 60. Pulse wave amplitude processing program which is able to control the blood pressure measuring adaptor 50, to receive data detected by the blood pressure measuring adaptor 50, to form measurement patterns of pulse wave amplitudes by processing said data, and further to judge to which one or more of a plurality of reference pattern groups the formed measurement pattern belongs, is installed in one of these operating systems. The program is stored in one of various kinds of memory devices which can be recognized by the central processing unit of the personal computer.

It is possible to connect various kinds of input operation devices such as a keyboard 80 shown in FIG. 3 or a mouse, etc. to the personal computer 60 as necessary. Furthermore, it is also possible to connect various kinds of display and output devices such as a display 70 shown in FIG. 3 or printer, etc. thereto.

Figure 1:
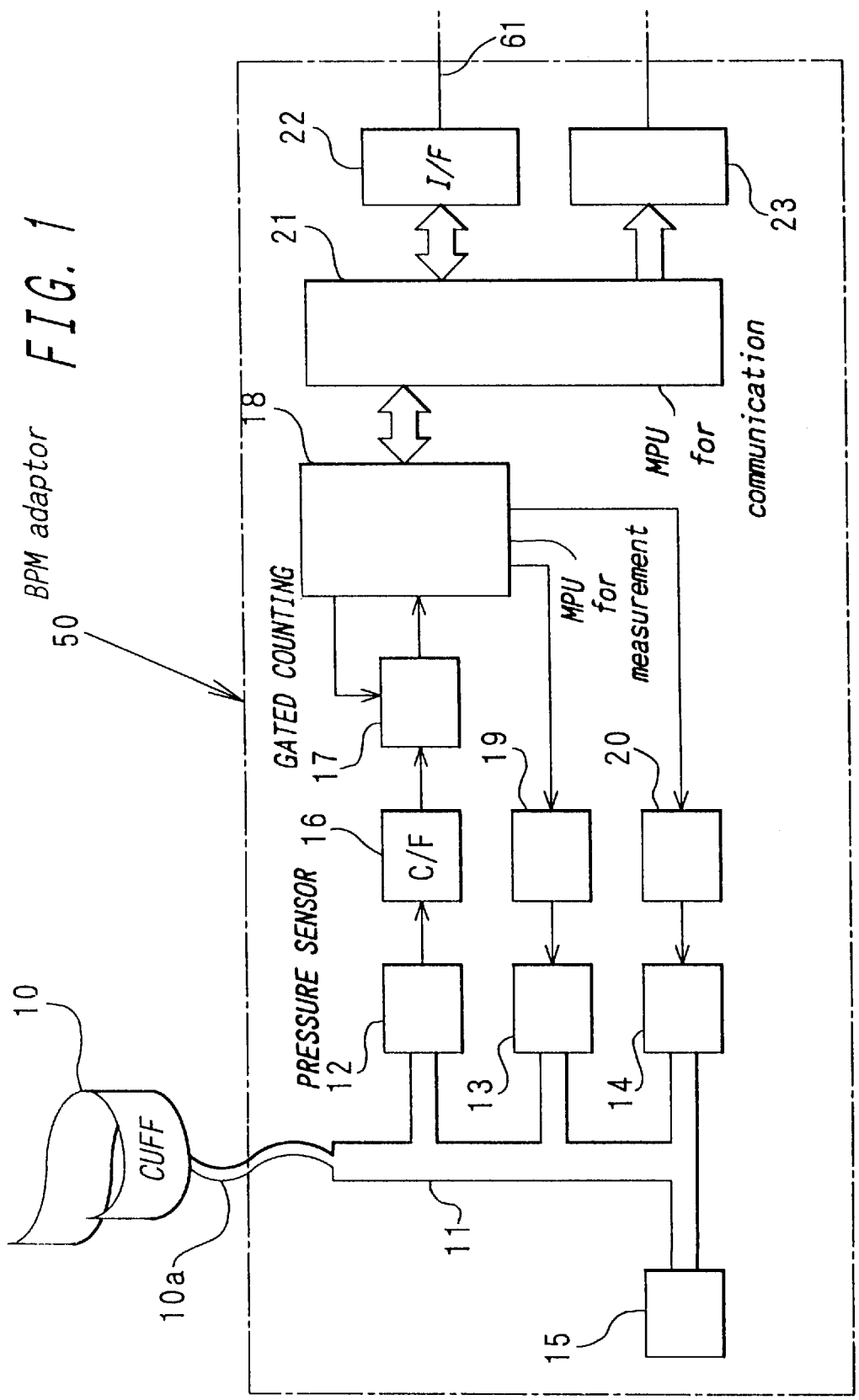
FIG. 1 is a block diagram showing a brief construction of a blood pressure measuring adaptor used for a preferred embodiment of the invention.

FIG. 1 shows a hardware construction of said blood pressure measurement adaptor 50. A cuff 10 is inflatable and such that it is band-like so that the same can be wound on an arm of a patient, and a flexible air tube 10a is connected to this cuff 10.

Said air tube 10a is connected to the inner pipe 11 of the blood pressure measurement adaptor 50. An electrostatic type pressure sensor 12, a forced air exhaust valve 13, a compression pump 14 to supply air, and a leak valve 15 to slowly exhaust air from the cuff 10 are connected to this inner pipe 11.

Said sensor 12 is connected to a capacity-frequency conversion circuit 16, and said capacity-frequency conversion circuit 16 converts the signal potential received from the pressure sensor 12 to pressure detection signals having a frequency corresponding to the cuff pressure. The pressure detection signals(pulses) are counted at every appointed duration of time by a gated counting circuit 17, and the counted values are inputted into a microprocessor unit 18.

The microprocessor unit 18 sends out a gate signal to the gated counting circuit 17 at every appointed duration of time, for example, once every 50 milliseconds. Furthermore, the microprocessor unit 18 sends out a control signal to an exhaust valve drive circuit 19 in order to open and close the forced exhaust valve 13 at an appointed timing and also sends out another control signal to a pump drive circuit 20 in order to adequately actuate the compression pump 14 consisting of a rolling pump.

Said microprocessor unit 18 is provided with a central processing unit, a read only memory (ROM) in which basic operation programs and various kinds of parameters are incorporated, and a random access memory (RAM) for storing necessary data during the operation. This microprocessor unit 18 is for controlling the drive system and detection system for measurement of blood pressure and for computing the blood pressure value, and further sends out a gate signal to the gated counting circuit 17 in order to take in data and sends out another control signal to the exhaust valve drive circuit 19 in order to open and close the forced exhaust valve 13. Furthermore, the microprocessor unit 18 also sends out a control signal to the pump drive circuit 20 in order to drive and stop the compression pump 14.

The microprocessor unit 18 is connected to another microprocessor unit 21 for communication, which is provided inside the blood pressure measurement adaptor 50. The microprocessor unit 21 is constructed so that the same receives instructions (commands) from the personal computer 60 through an interface circuit 22 via a connection cable 61 and reversely sends out data codes and status codes to the personal computer 60 through the interface circuit 22. The microprocessor unit 21 includes a central processing unit for computation processes, a ROM in which basic operation programs and various kinds of parameters are installed, and a RAM for storing necessary data during the operation. In this RAM, a transmission buffer and a receiving buffer, which are able to temporarily store communication data when a communication with the personal computer 60 is carried out, are provided.

The microprocessor unit 21 is connected to the output circuit 23, and the output circuit 23 is constructed so that data can be outputted to display and output devices such as a display 70, a printer, etc. The microprocessor unit 21 sends out action instructions and measurement parameters to be used in blood pressure measurement to the microprocessor unit 18 upon receiving an instruction from the personal computer 60. Furthermore, the microprocessor unit 21 receives a series of cuff pressure data, a series of pulse wave amplitude data, maximum blood pressure value, mean blood pressure value, minimum blood pressure value, pulse rate, etc. from the microprocessor unit 18 and sends the same to the personal computer 60 one after another by the method described below, on the base of instructions coming from the personal computer 60.

Figure 2:
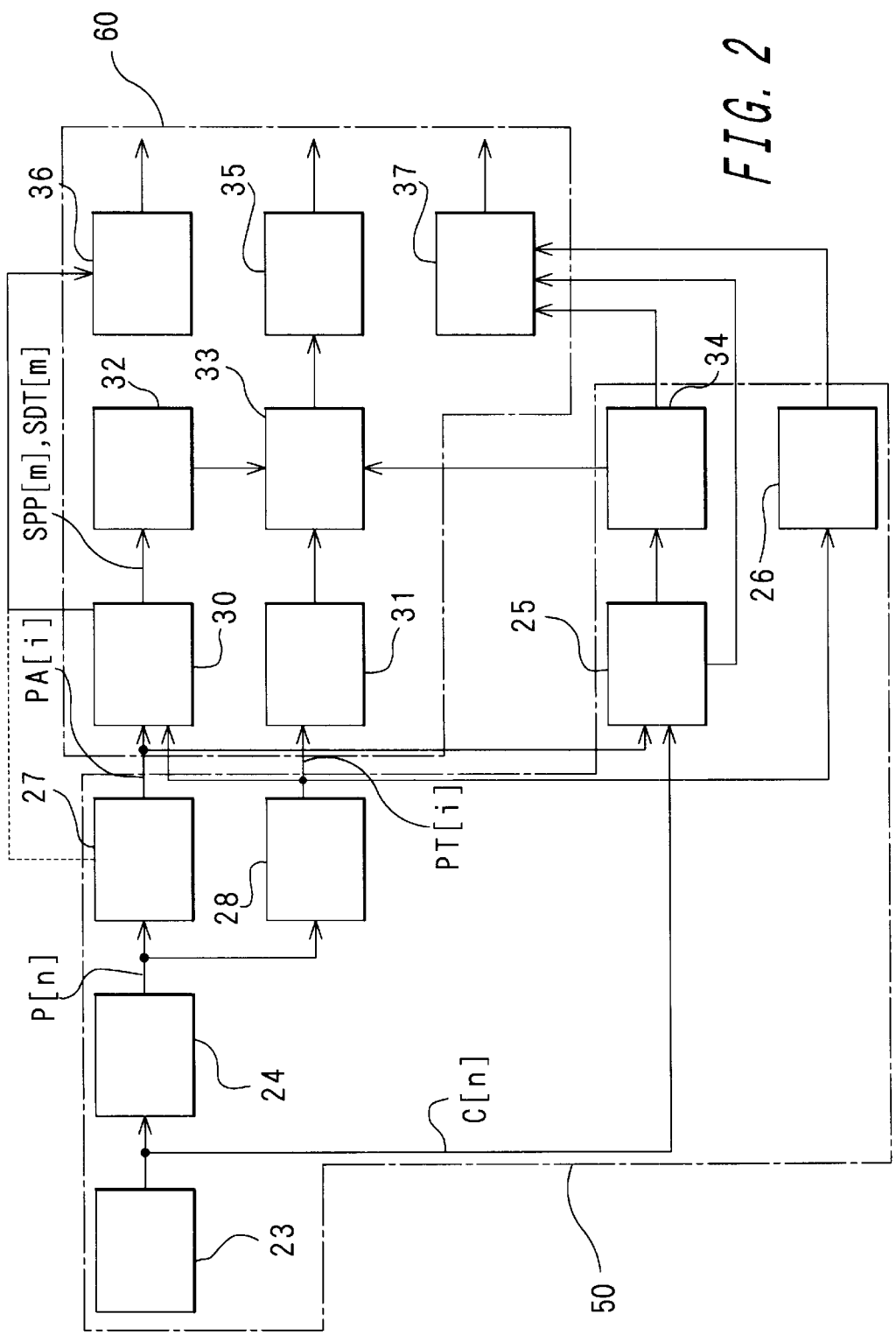
FIG. 2 is a block diagram showing means for achieving functions realized by a blood pressure measuring adaptor and the pulse wave amplitude processing program operated by a personal computer used for the preferred embodiment of the invention.

FIG. 2 illustrates a plurality of means for achieving functions which are embodied in the entire system consisting of a cuff 10 and a blood measurement adaptor 50, which are shown in FIG. 1, and a personal computer 60 shown in FIG. 3. A cuff pressure detection means 23 is mainly accomplished by a cuff 10 shown in FIG. 1, the pressure sensor 12, the capacity-frequency conversion circuit 16, the gated counting circuit 17 and the microprocessor unit 18. The cuff pressure which is compressed to an appointed pressure level by a compression pump 14, and then is caused to decrease by air leaking little by little out of the cuff 10 by the leak valve 15. The cuff pressure detection means is constructed so that the cuff pressure is detected by the pressure sensor 12 and the capacity-frequency conversion circuit 16, and this signal detected is counted by the gated counting circuit 17 and is taken into the microprocessor unit 18 as digital data at every appointed duration of time (for example, once every 50 milliseconds) by a gate signal of the microprocessor unit 18.

A series of data C[n] (Data number n=1,2,3, . . .) (hereinafter called "( (a series of) cuff pressure data") detected and taken in as described above are values (digital values) which shows fluctuations shown by a graph (a) in FIG. 4. This series of cuff pressure data C[n] is converted to a series of differential data P[n] (corresponding to differential signal of the cuff pressure signal) shown by a graph (b) in FIG. 4, inside the microprocessor unit 18. The series of differential data P[n] is further converted to a series of extracted differential data P'[n] which corresponds to the differential wave form based on only the pulse wave signal constituents by eliminating the contribution of the mean decreasing rate (corresponding to the inclination of graph (a) in FIG. 4) of the series of cuff pressure data C[n]. These computation processes are performed in the microprocessor unit 18 and composes a pulse wave extracting means 24 shown in FIG. 2. Furthermore, it is possible to obtain pulse wave data by a method for extracting pulse wave constituents by detecting the cuff pressure as analog signals and carrying out differential and integration computations which are different from those described above, a method for directing extracting pulse wave constituents by giving a band-pass filter process to the cuff pressure signals, or other methods equivalent thereto.

Next, by computing the values in the domains which have a positive value in the series of extracted differential data P'[n] at every pulse wave in the pulse wave amplitude computing means 27 shown in FIG. 2 (which is equivalent to integration of differential signals), the series of pulse wave amplitude value data PA[i] (pulse wave number i=1, 2,3, . . .) can be computed. Furthermore, the time data at the zero-cross point P0 (the point where the value of P'[n] changes from positive to negative and which corresponds to the peak point of pulse wave signals) for every pulse wave at the series of extracted differential data P'[n] is computed as a series of pulse wave time data PT[i] in the pulse wave time computing means 28 shown in FIG. 2.

The processes in said pulse wave amplitude computing means 27 and pulse wave time computing means 28 are carried out in the microprocessor unit 18. The series of pulse wave amplitude value data PA[i] and the series of pulse wave time data PT[i] compose the digital data showing a fluctuation process of the pulse wave amplitude in the process during which the value of the cuff pressure data C[n] is caused to decrease, that is, sets of the pulse wave amplitude data. The sets of pulse wave amplitude data are computed one after another in the process during which the cuff pressure is gradually decreased. Next, they are transferred from the microprocessor unit 18 to the microprocessor 21 one after another. And then, they are stored in a memory device of the microprocessor unit 21.

In the microprocessor unit 18, the maximum value PAmax of the series of pulse wave amplitude value data PA[i] is detected, and then the series of cuff pressure data C[n] at the point where this PAmax value is obtained is computed as the mean blood pressure value Pmean. This means constitutes a mean blood pressure computing means 25 shown in FIG. 2.

Next, the pulse wave amplitude value PAhi having the closest value to the value of an appointed ratio S(%) of the maximum value PAmax, which is the pulse wave amplitude value PA[i] corresponding to a higher cuff pressure value than the value of the cuff pressure data at the point of time the maximum value PAmax of the pulse wave amplitude obtained by the mean blood pressure computing means 25, is obtained, and the value of the cuff pressure data C[n] at the point where this pulse wave amplitude value PAhi is obtained is calculated as the systolic blood pressure Psyst. This means also constitutes a blood pressure calculating means 34 shown in FIG. 2. With the blood pressure calculating means 34, the pulse wave amplitude value PAlo having the closest value to the value of an appointed ratio D(%) of the maximum value PAmax, which is the pulse wave amplitude value data PA[i] corresponding to a lower cuff pressure than the cuff pressure at the point when the maximum value PAmax of the pulse wave amplitude is obtained, and the value of the cuff pressure data C[n] at the point of time when said pulse wave amplitude value PAlo is obtained is computed as the diastolic blood pressure value Pdias. The respective values of S% and D% of said appointed ratios are adequately set so that a blood pressure value as correct as possible can be calculated by comparing a stethoscopic method (method for calculating the blood pressure value by Korotkoff's sounds) with a direct method (method for directly calculating the inner pressure by inserting a catheter, etc. into a blood vessel).

The pulse rate computing means 26 shown in FIG. 2 is used to obtain the mean value of the pulse rates in the duration of measurement described later, on the basis of the series of pulse wave time data PT[i] secured by the pulse wave time computing means 28 and outputs the same as the pulse rate PR.

Although said series of cuff pressure data C[n], pulse wave amplitude value data PA[i], and pulse wave time data PT[i] are calculated one after another during the measurement, the measurement is finished when the diastolic blood pressure value Pdias is computed by the blood pressure value computing means 34, and finally the pulse rate is calculated by the pulse rate computing means 26, whereby a series of processes are completed.

On the other hand, the microprocessor unit 21 receives, as described later, the series of cuff pressure data C[n], pulse wave amplitude value data PA[i], pulse wave time data PT[i], systolic blood pressure value Psyst, mean blood pressure value Pmean, diastolic blood pressure Pdias and pulse rate PR from the microprocessor unit 18, temporarily stores the same in memory, and transfers the same to the personal computer 60 on the basis of instructions of the personal computer 60.

The personal computer 60 interpolates the pattern shape by a spline curve after eliminating noise of the sets of pulse wave amplitude data on the basis of the series of pulse wave amplitude value data PA[i] and pulse wave time data PT[i] and smoothing the fluctuation state of the pulse wave amplitude values, and further normalizes the scale showing the amplitude value of the fluctuation pattern shape of the pulse wave amplitude values obtained by the interpolation of the spline curve and the scale showing the time thereof, whereby a measurement pattern is formed. This measurement pattern is expressed with the series of the normalized amplitude data SPP[m] and the series of normalized interval data SDT[m]. This process is shown for a measurement pattern forming means 30 in FIG. 2.

Furthermore, the personal computer 60 detects disorder of pulse waves from the series of pulse wave time data PT[i]. This process is shown as a disorder detecting means 31 shown in FIG. 2, which detects the degree of timing irregularities of pulse wave generation. On the other hand, on the basis of the normalized amplitude data SPP[m] and normalized interval data SDT[m], which are formed in the measurement pattern forming means 30 and show measurement patterns, the position and height of one or more peaks in the measurement pattern and other features regarding the peak shape are detected in the peak shape detecting means 32. The disorder detecting means 31 and peak shape detecting means 32 are used to extract the feature of measurement patterns or pulse wave amplitude data and constitute a feature point extracting means.

Finally, on the basis of the features obtained by the disorder detecting means 31 and the features obtained by the peak shape detecting means 32, a pattern judging means 33 judges to which one or more reference pattern groups of a plurality of reference pattern groups shown in FIG. 7 the measurement pattern belong, wherein the blood pressure value secured by a blood pressure value computing means 34 is also utilized as a part of the features. The pattern judging means 33 holds a plurality of parameters pertaining to the reference pattern groups in advance, compares said features with said plurality of parameters and determines to which one or more reference pattern groups the secured measurement pattern belongs.

The result of judgement obtained by said pattern judging means is displayed on a display by the pattern judgement display and output means 35 shown in FIG. 2 or printed out by a printer, etc. Furthermore, the fluctuation state of the pulse wave amplitude obtained by the pulse wave amplitude data or the measurement pattern shape formed by the measurement pattern forming means 30 are displayed on a display by the measurement pattern display and output means 36 or printed out by a printer. Still furthermore, the systolic blood pressure value Psyst, mean blood pressure value Pmean, diastolic blood pressure value Pdias and pulse rate PR which are respectively obtained by the mean blood pressure computing means 25, blood pressure computing means 34, and pulse rate computing means 26 are displayed or outputted by the blood pressure value display and output means 37.

Figure 11:
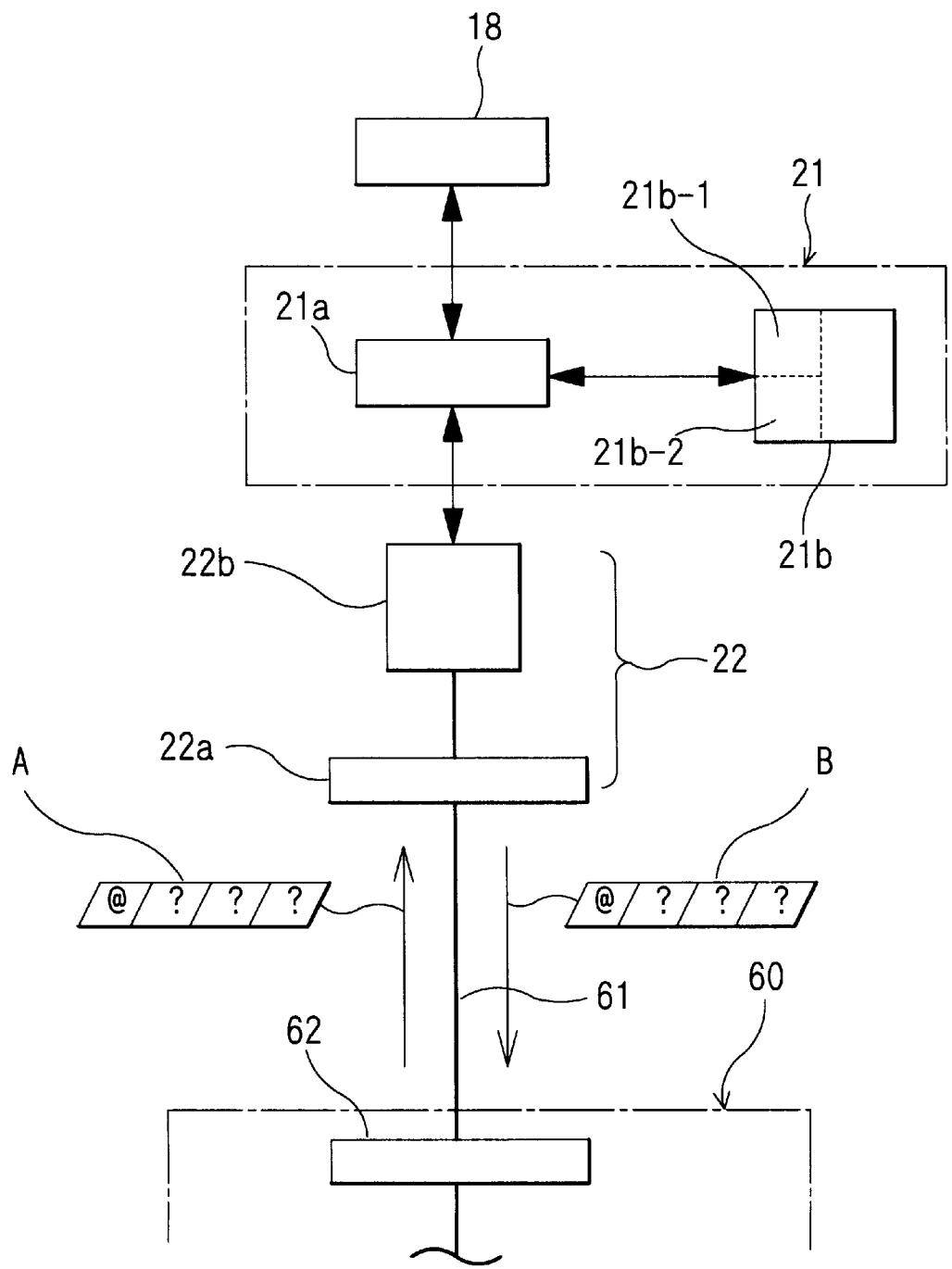
FIG. 11 is a block diagram showing a brief construction of the section pertaining to the communication between the blood pressure measurement adaptor and personal computer.

FIG. 11 is an brief construction view showing a part of the blood pressure measurement adaptor 50 and a part of the personal computer 60, pertaining to the communication between the blood pressure measurement adaptor and the personal computer. The microprocessor unit 21 is used for communication and control and is provided with a central processing unit 21a and a memory (RAM) 21 b. A 64-byte transmission buffer 21b-1 and a 64-byte receiving buffer 21b-2 are secured in the memory 21b. An RS232C input and output circuit 22a and an RS232C buffer memory 22b are provided in the interface circuit 22. On the other hand, an input and output circuit 62 is also provided at the personal computer 60 side. With such a structure, communication by which commands (instructions) and data transmission or receiving between the blood pressure adaptor 50 and personal computer 60 are carried out.

The communication between the blood pressure measurement adaptor 50 and personal computer 60 is interactive and is carried out by the unit of frames A and B each consisting of a 4-byte serial data row. Each byte in the frames A and B is composed of 8 bits. A start code consisting of a character code "@" is always disposed in the beginning byte area. Character codes showing the preset commands, operating status of the apparatus and the kind of data and other binary data which show various kinds of measurement values are arranged in the remaining three byte areas.

Figure 12:
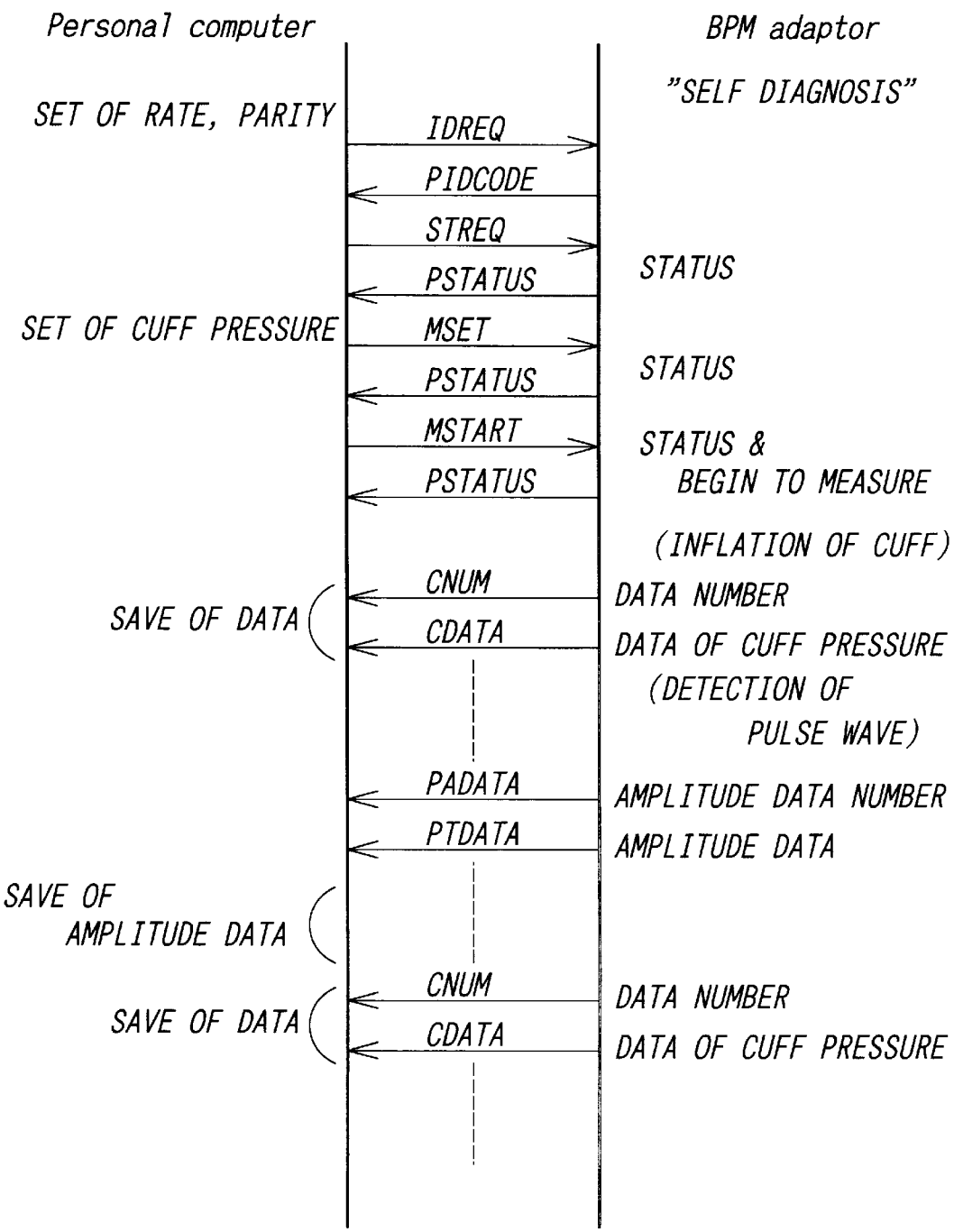
FIG. 12 and FIG. 13 are timing charts showing the process of the communication procedure between the blood pressure measurement adaptor and personal computer.
Figure 13:
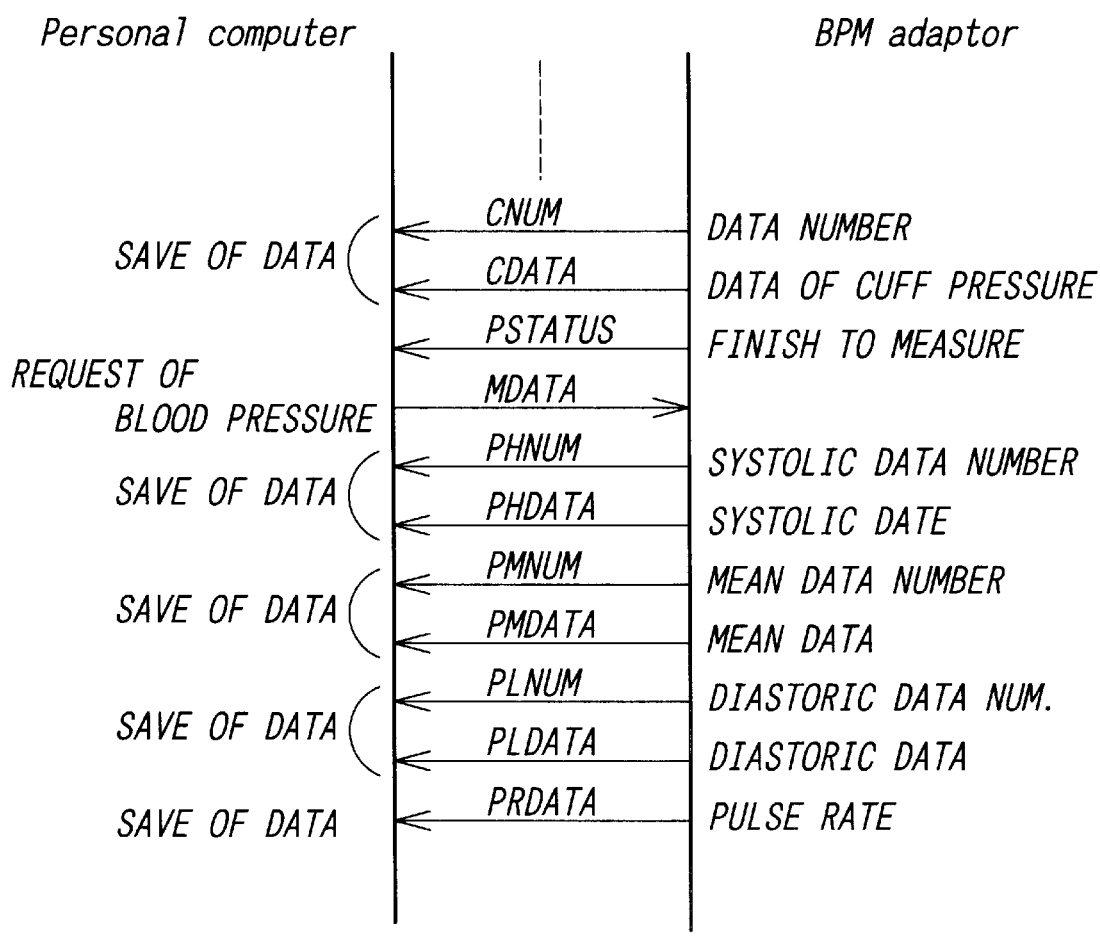

FIG. 12 and FIG. 13 show the exchange of codes or data between the blood pressure measurement adaptor 50 and the personal computer 60. As shown in FIG. 12, if the power source of the blood pressure adaptor 50 is turned on, the blood pressure measurement adaptor 50 executes a self diagnosis for about one minute on the basis of a self diagnosis program stored in a ROM of the microprocessor unit 18. This self diagnosis is for checking each operating state of the drive system, measurement system and communication system in the blood pressure measurement adaptor.

With the self diagnosis completed, the personal computer 60 reads the communication speed and parity established in the blood pressure adaptor 50 and sets the self communication states. Next, since the personal computer 60 sends out an ID confirmation request command IDREQ in order to confirm a connection with the blood pressure adaptor, the blood pressure adaptor 50 sends back an identification code PIDCODE of the blood pressure adaptor upon receiving the IDREQ. Next, since the personal computer 60 sends out a status request command STREQ in order to know the status of the blood pressure measurement adaptor, the blood pressure measurement adaptor 50 transmits an interior status PSTATUS and informs the personal computer 60 of the measurement status and communication status. When it is confirmed with this interior status that the blood pressure measurement adaptor is not during a measurement, the personal computer 60 displays on its display 70 that the measurement is enabled.

Still furthermore, since the personal computer 60 sends out a compression setting command MSET including compression setting information, the blood pressure measurement adaptor 50 establishes the compression setting value of the microprocessor unit 18 as per instruction of the personal computer 60, and thereafter the interior status PSTATUS is sent back. The personal computer 60 sends out a compression setting command again in a case where an error occurs in the command receiving due to a content of the interior status.

Next, as the measurement commencement is operated by an input device of the personal computer 60, the personal computer 60 sends out a measurement commencement request command MSTART and the blood pressure measurement adaptor 50 commences a measurement after sending back the interior status, wherein the blood pressure measurement adaptor 50 shuts the forced exhaust valve 13 and simultaneously starts the compression pump 14 to raise the pressure of the cuff 10 up to the appointed compression setting value. As the measurement is commenced, the blood pressure measurement adaptor 50 sends out the series of cuff pressure data detected once every 50 milliseconds as pressure data number CNUM (=n) and pressure data CDATA (=C[n]) one after another. Furthermore, since the pulse wave amplitude value data PA[i] and pulse wave time data PT[i] are calculated by the microprocessor unit 18, the blood pressure adaptor 50 sequentially sends them out as pulse wave amplitude data PADATA and pulse wave time data PTDATA while the transmission of CNUM and CDATA is interrupted. The pulse wave amplitude value data PADATA and pulse wave time data PTDATA include the respective data number (=i).

Said cuff pressure data C[n], pulse wave amplitude value data PA[i] and pulse wave time data PT[i] are stored as data in an appointed recording device after being received by the personal computer 60. As the measurement is finished by the blood pressure adaptor 50, the blood pressure measurement adaptor 50 sends out the interior status PSTATUS and informs that the measurement has been finished. Upon receiving this, the personal computer 60 sends out a blood pressure measurement value request command MDATA. The blood pressure measurement adaptor 50 sends out the systolic blood pressure value number PHNUM (=n) which is the data number at the point when the systolic blood pressure value is obtained and systolic blood pressure value data PHDATA, the mean blood pressure value number PMNUM (=n) which is the data number at the point when the mean blood pressure is obtained and mean blood pressure value data PMDATA, and the diastolic blood pressure value number PLNUM(=n) which are the data numbers at the point when the diastolic blood pressure value is obtained and diastolic blood pressure value data PLDATA, and the pulse rate data PRDATA showing the pulse rate PR.

As described above, various kinds of measurement data which are measured and calculated by the blood pressure measurement adaptor 50, that is, the series of cuff pressure data C[n], the series of pulse wave amplitude value data PA[n], the series of pulse wave time data PT[i], systolic blood pressure value Psyst, mean blood pressure value Pmean, diastolic blood pressure value Pdias and pulse rate PR are transferred to the personal computer 60, wherein they are respectively stored in a recording device.

Figure 14:
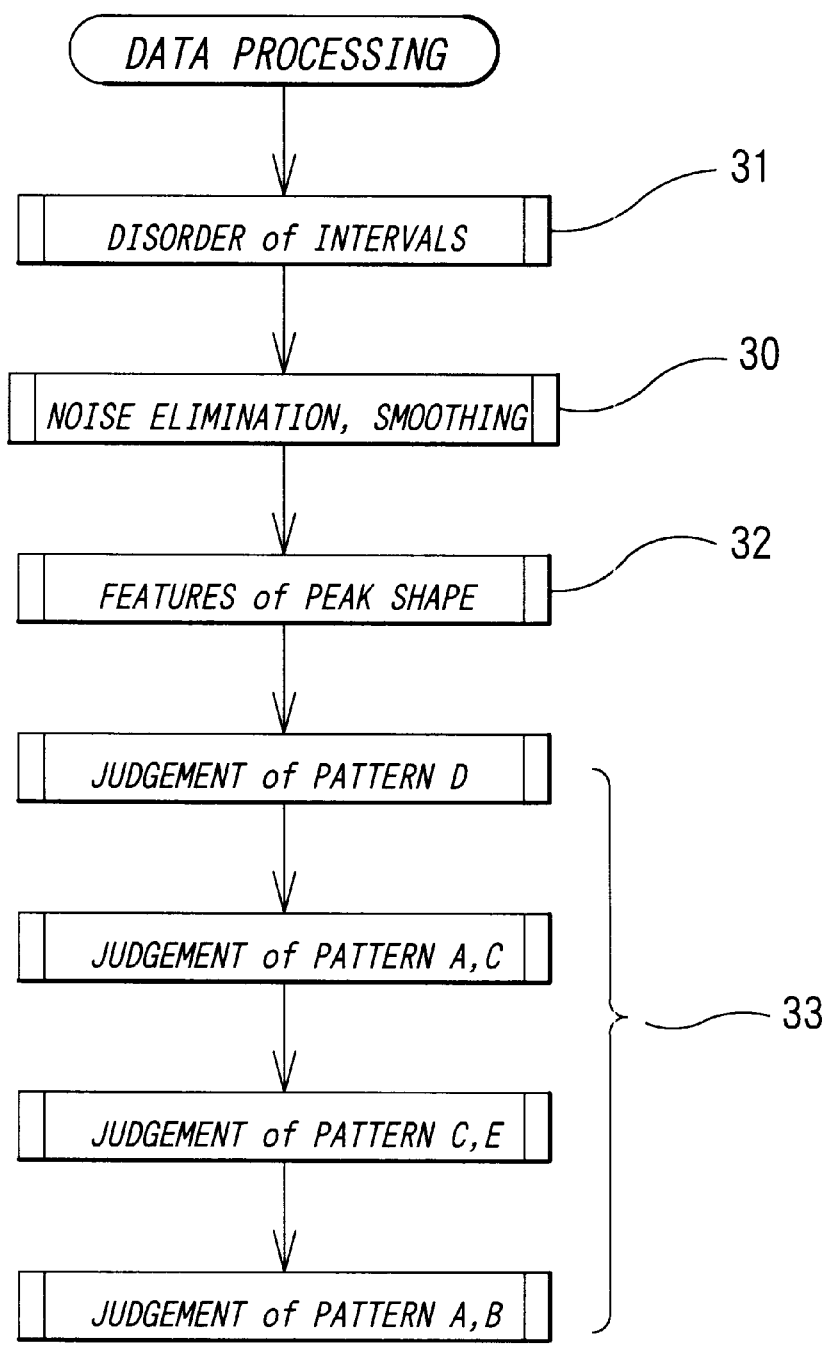
FIG. 14 is a flow chart showing a brief procedure of a pulse wave amplitude processing program driven by the personal computer.

FIG. 14 shows a flow of a data process which is carried out by the personal computer after the computer 60 reads in various kinds of measurement data. This data process is executed by being united to the respective means for achieving functions such as a measurement pattern forming means 30, disorder detecting means 31, peak shape detecting means 32 and pattern judging means 33 shown in FIG. 2. That is, FIG. 14 shows one example of the processes in a case where these means for achieving functions are realized one after another (step by step), wherein the reference numbers of the corresponding means for achieving functions shown in FIG. 2 are given at the right side for reference in FIG. 14.

As shown in FIG. 14, the personal computer 60 automatically detects disorder after it reads in the measurement data. Thereafter, the personal computer 60 forms a measurement pattern. Next, the personal computer 60 detects a peak shape and finally judge a pattern. The pattern judgement is carried out in the order of reference pattern group D, reference pattern groups A,C, reference pattern groups C,E and reference pattern groups A,B. Finally, the personal computer 60 determines to which one or more reference pattern groups the measurement pattern belongs.

FIG. 15 through FIG. 34 show the detailed processes shown in FIG. 14, which are executed by the personal computer 60.

Figure 15:
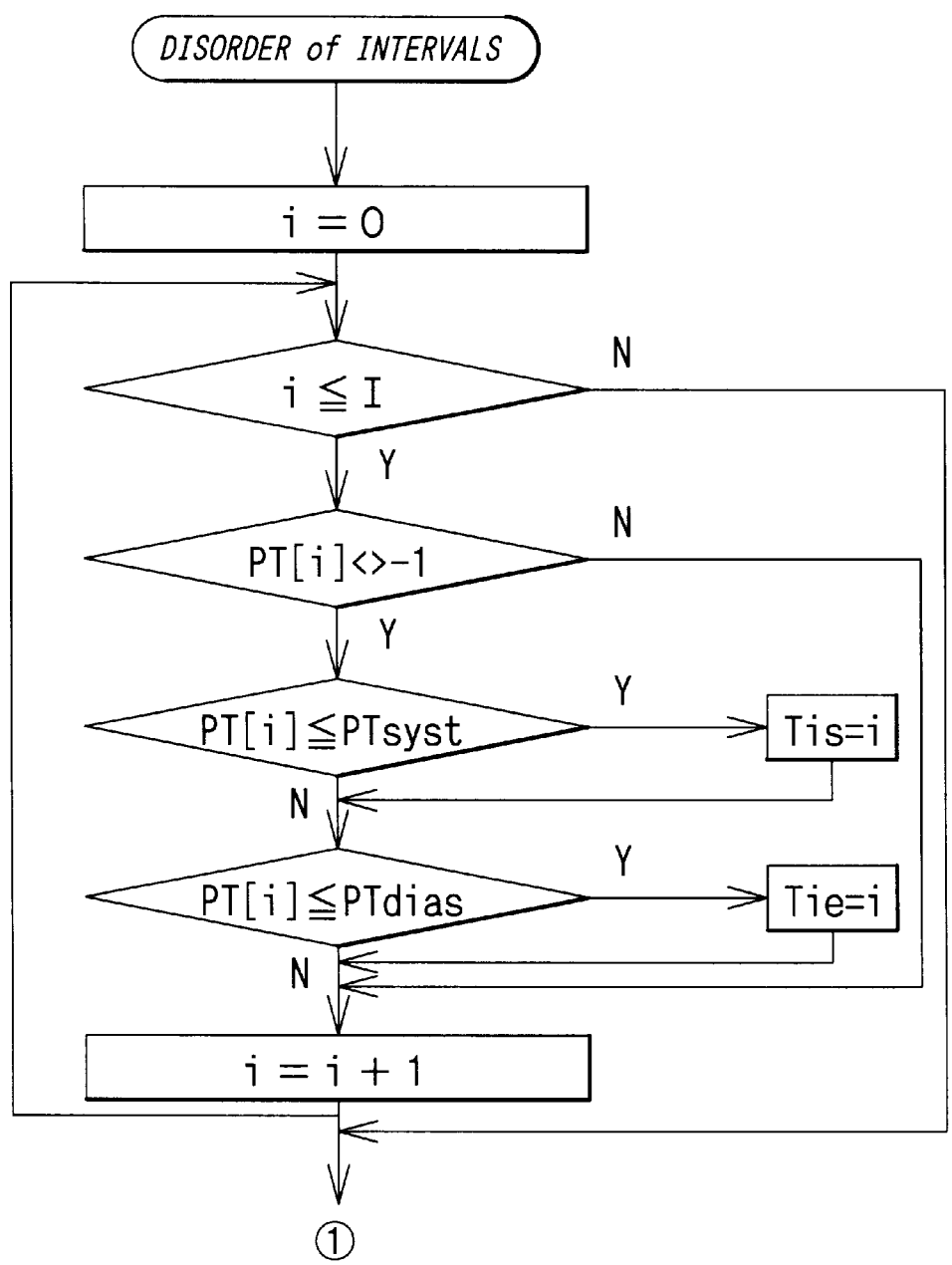
FIG. 15 and FIG. 16 are detailed timing charts showing the process steps of a part of the pulse wave amplitude processing program, which are a part of the feature extracting means and constitutes a means for detecting irregularities of the pulse wave intervals on the basis of the pulse wave amplitude data.

In the disorder detecting process, firstly, as shown in FIG. 15, the data scope for carrying out a process of pulse wave amplitude value data PA[i] and pulse wave time data PT[i]. In this step, unless the value of the pulse wave time data PT[i] is −1 at every data number i, the pulse wave time data PT[i] is compared with the time PTsyst at which the systolic blood pressure Psyst is measured, thereby determining the start data number Tis. And the pulse wave time data PT[i] is compared with the the time PTdias at which the diastolic blood pressure Pdias is measured, thereby determining the end data number Tie, wherein I is the final value when carrying out a measurement for the data number i, and the initial value of PT[i] in a memory device of the personal computer 60 is set to −1.

Figure 16:
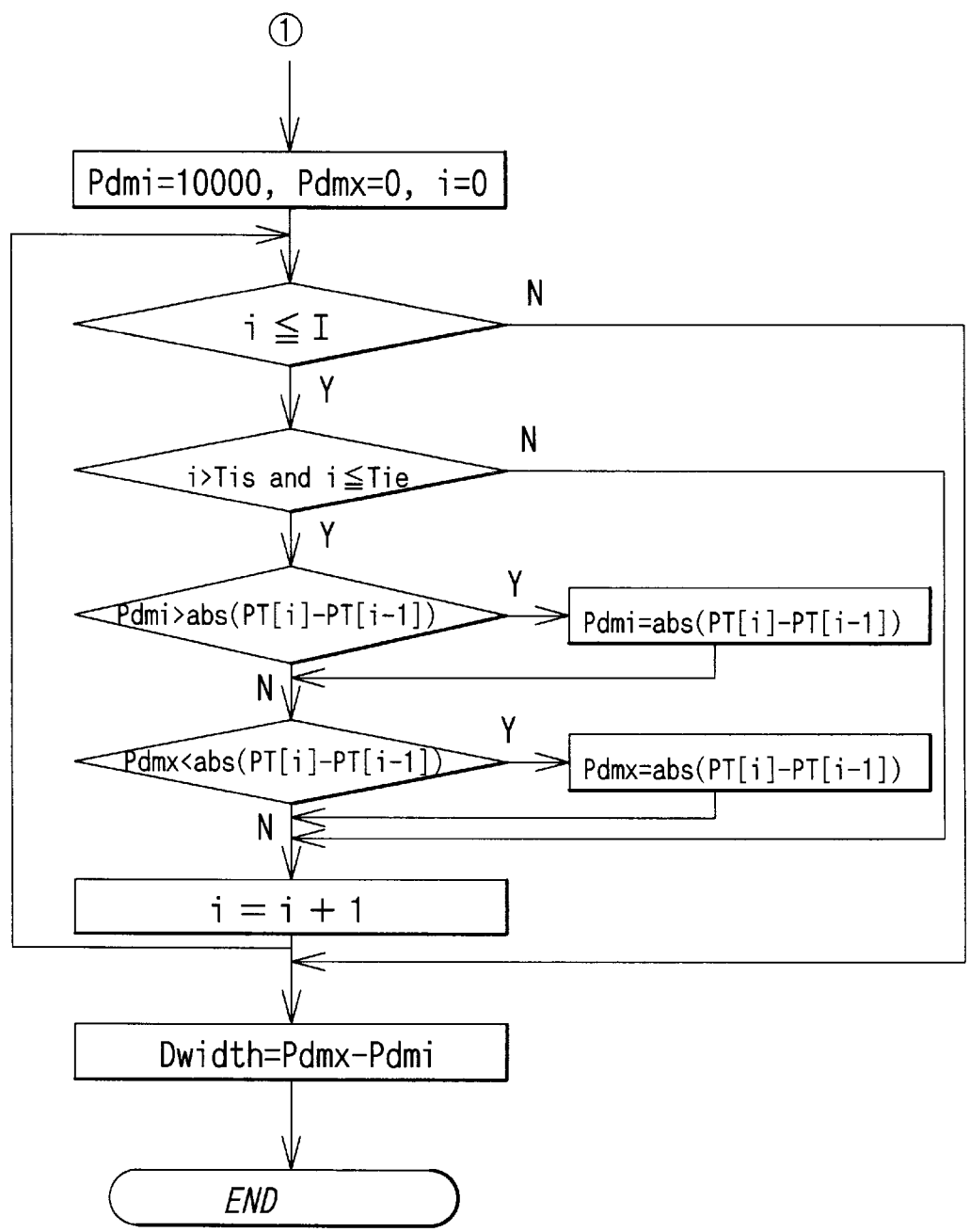

Next, as shown in FIG. 16, a series of pulse wave intervals is calculated on the basis of the pulse wave time data PT[i] in order to obtain the minimum value Pdmi and maximum value Pdmx of the pulse wave interval, thereby the maximum value of the difference of the pulse wave interval, Dwidth=Pdmi−Pdmx is calculated. The maximum value Dwidth shows the degree of irregularities in time as regards the pulse wave generation interval.

Figure 21:
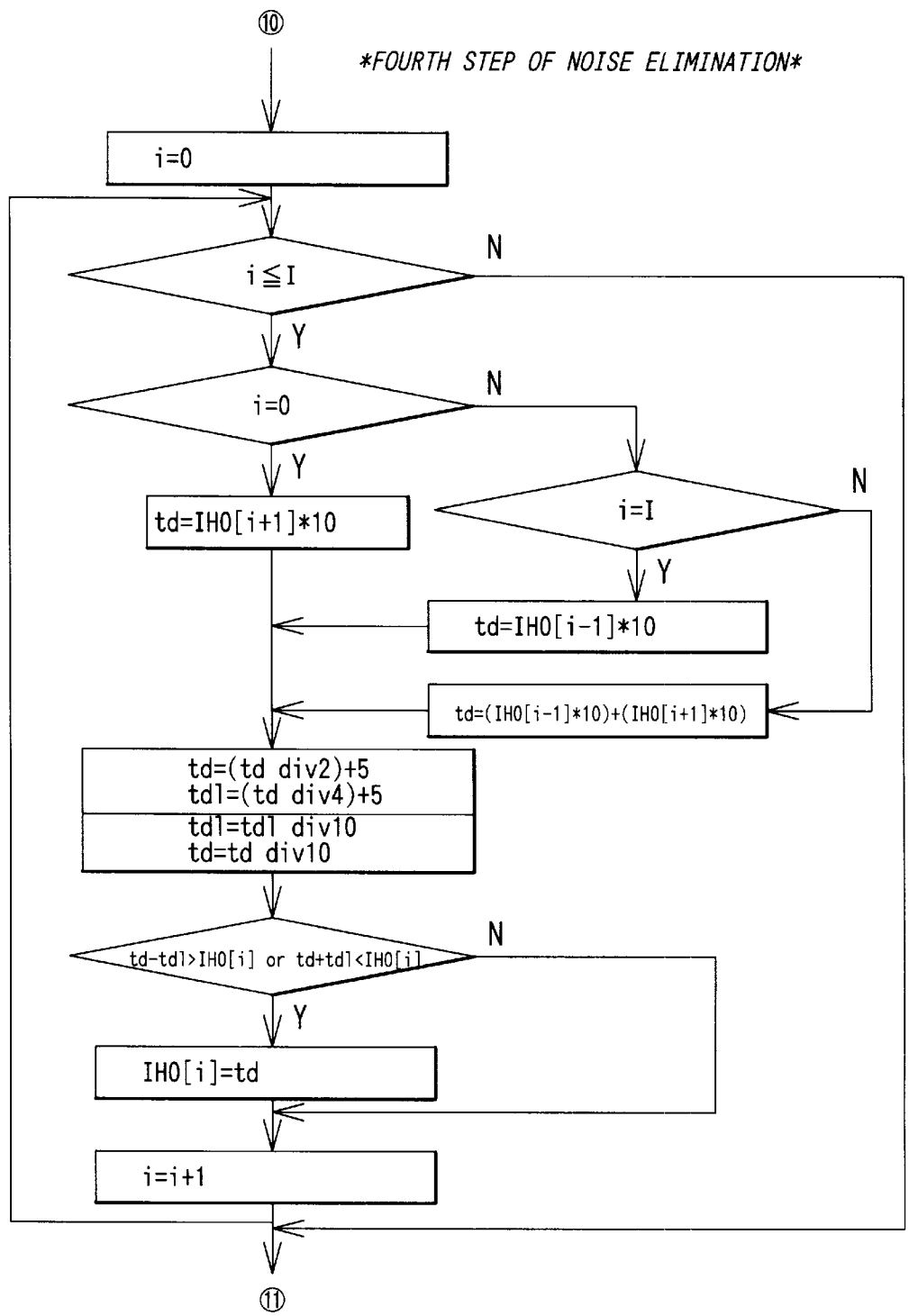
Figure 22:
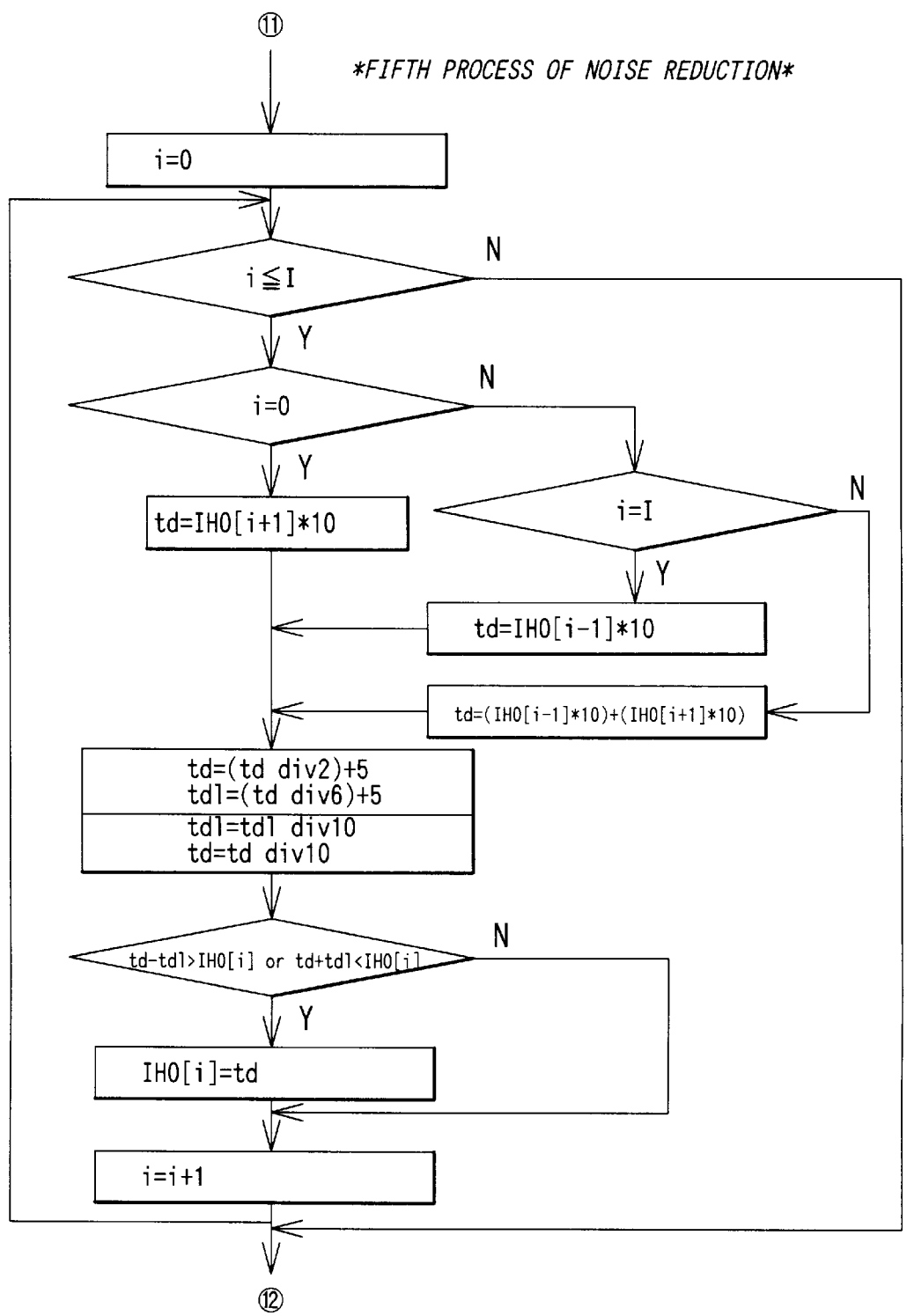
Figure 23:
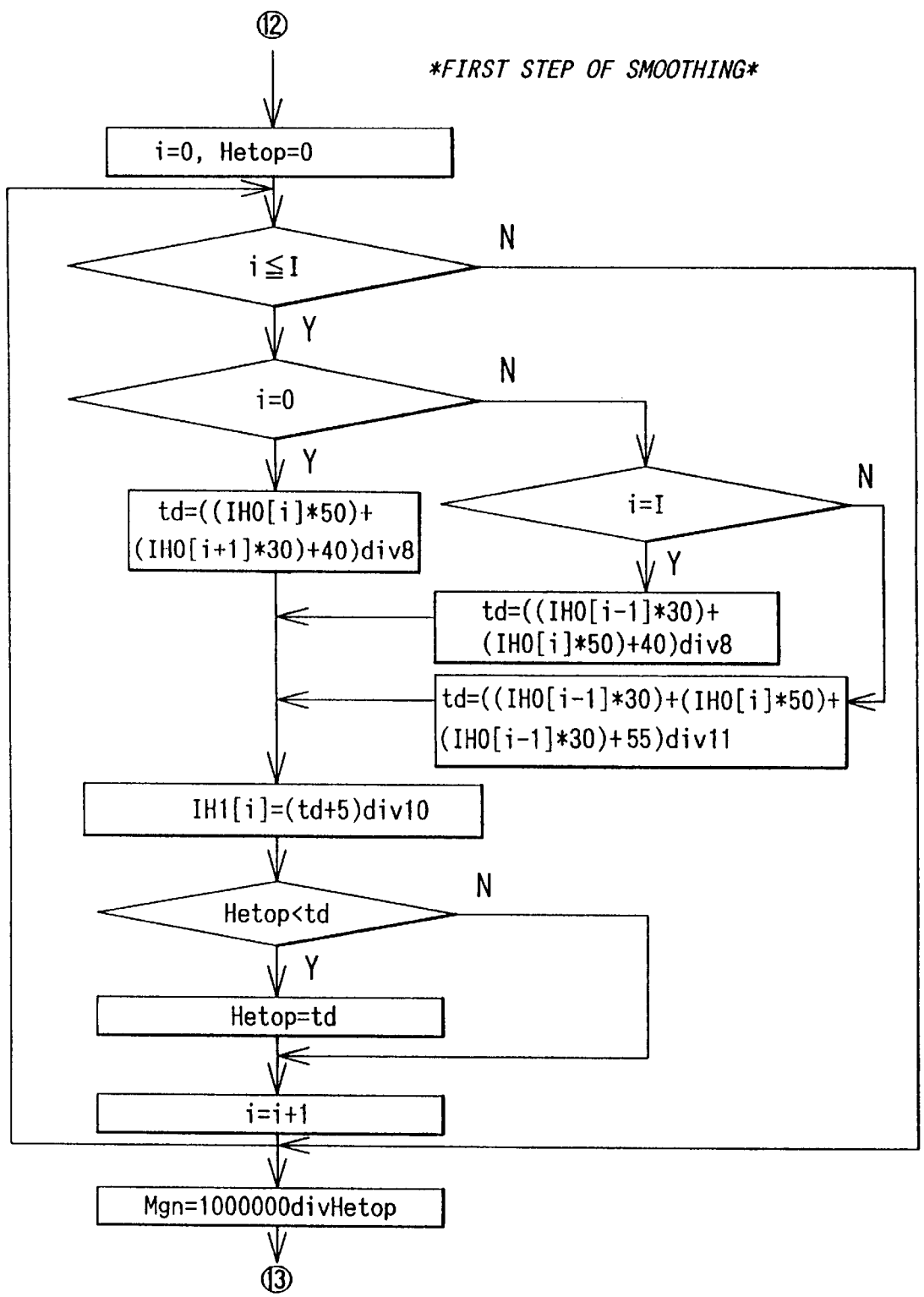
Figure 24:
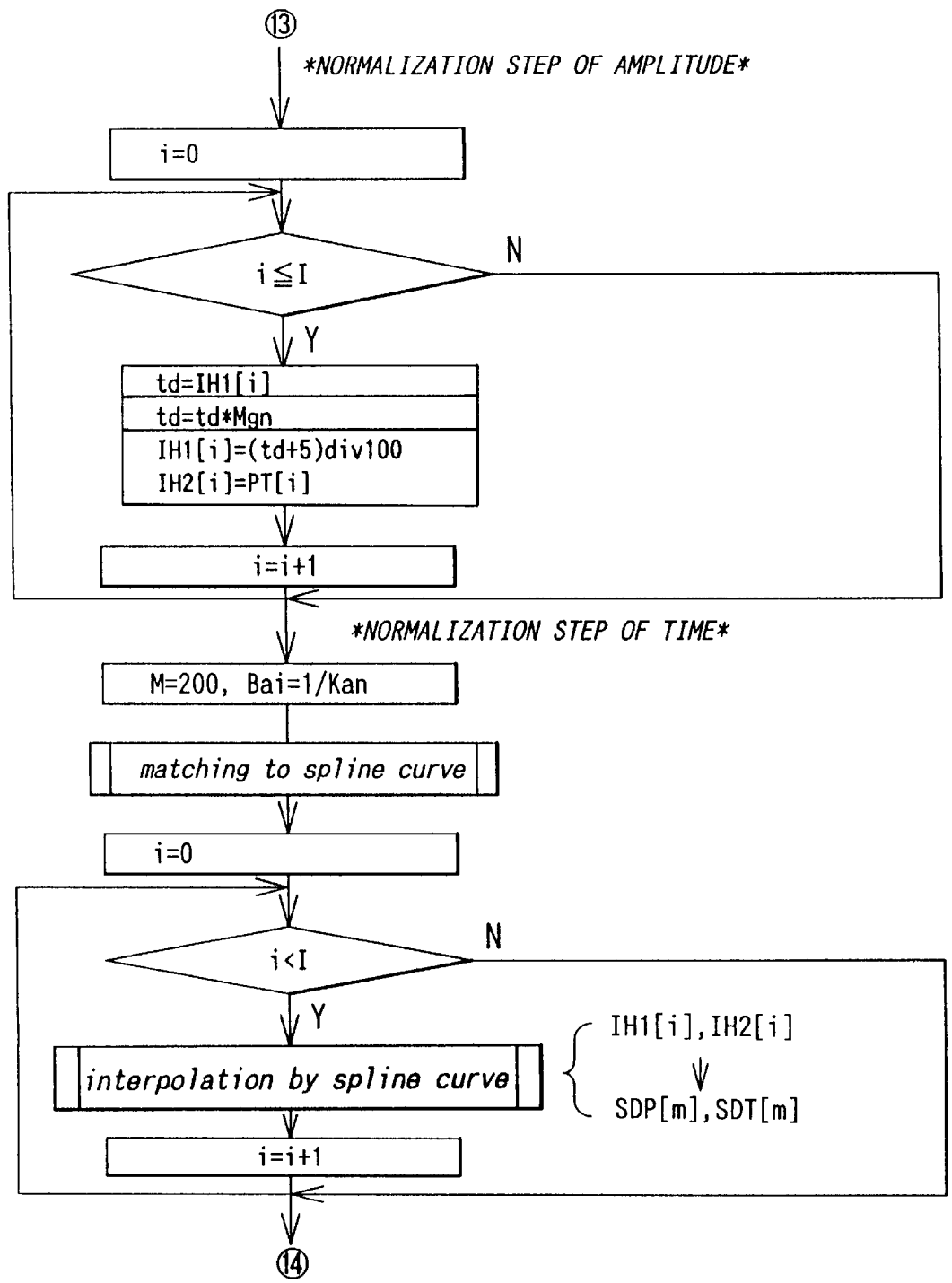
Figure 25:
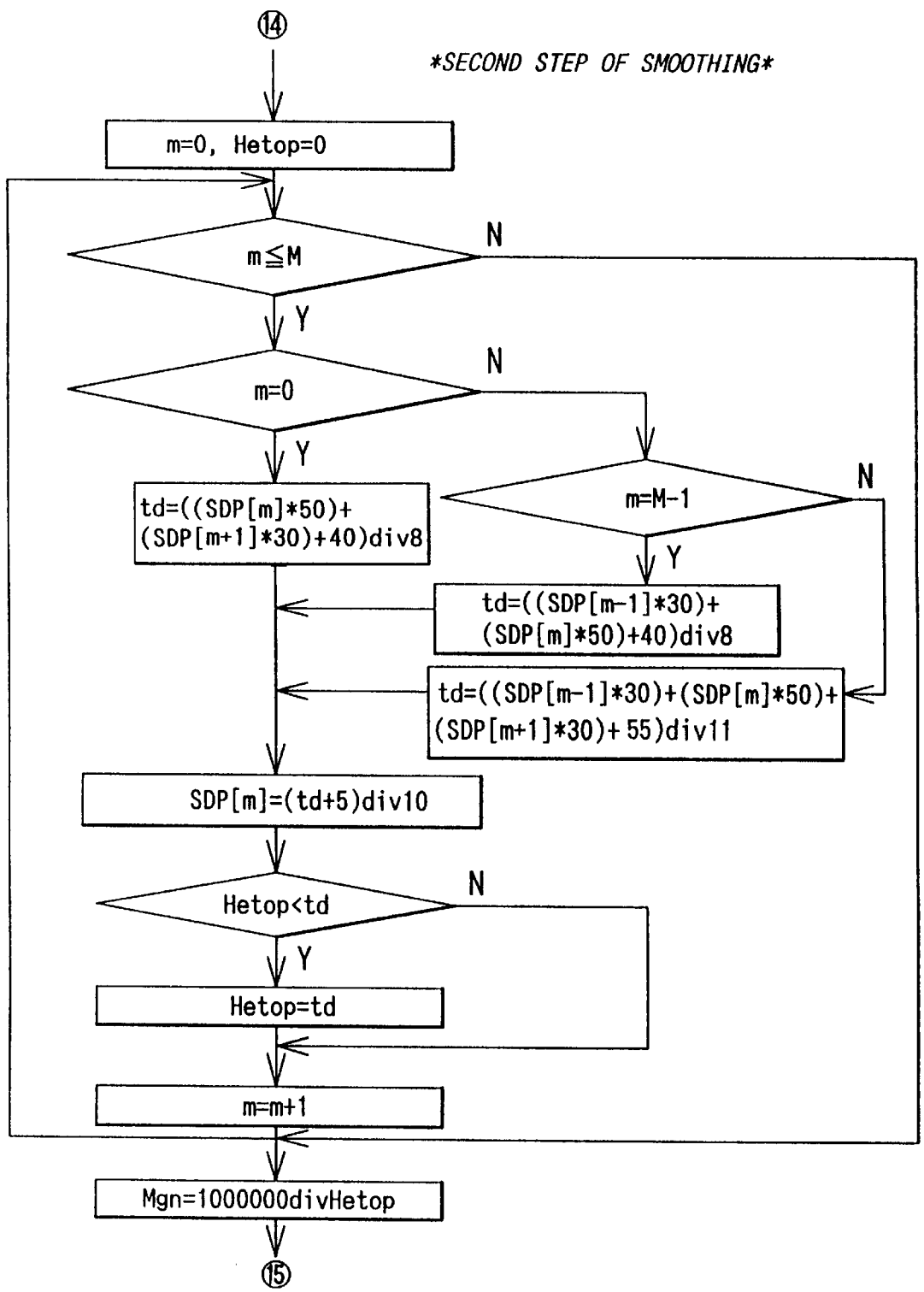
Figure 26:
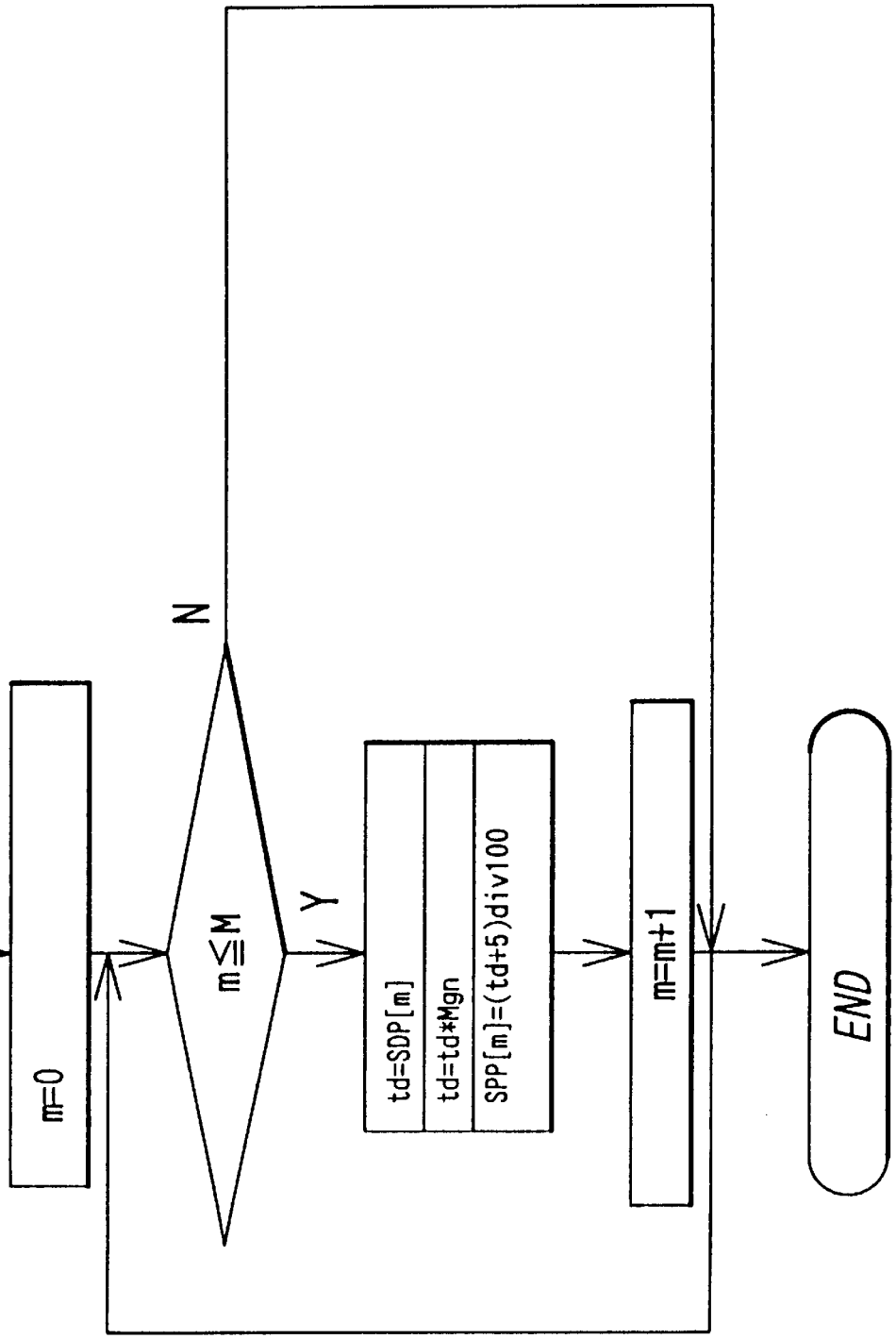

Next, in a measurement pattern forming process, steps for eliminating noise shown in FIG. 17 through FIG. 22, a process for smoothing the fluctuation pattern of pulse wave amplitudes shown in FIG. 23 through FIG. 25 and steps for normalizing patterns shown in FIG. 24 through FIG. 26 are carried out.

Figure 17:
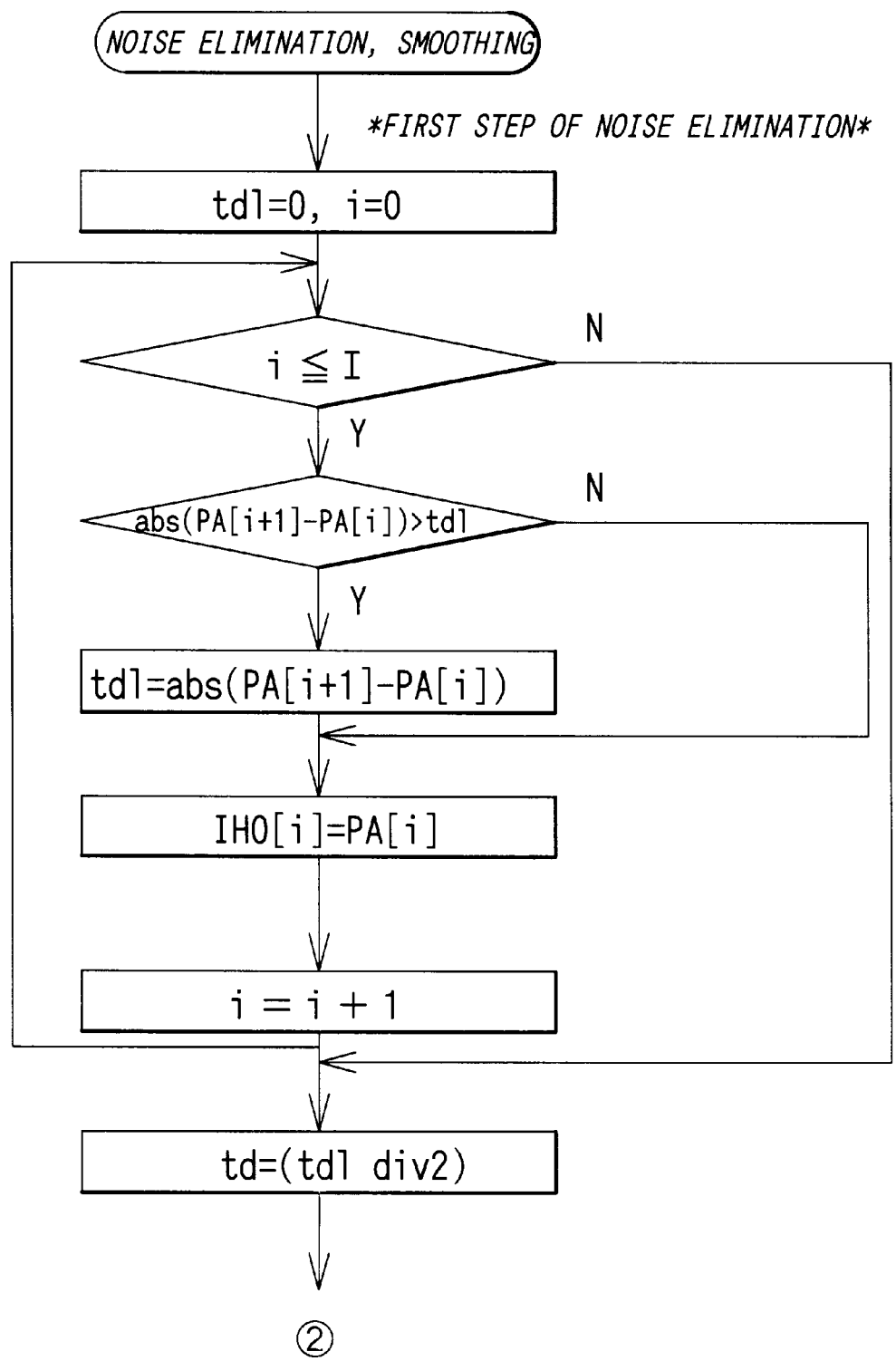
FIG. 17 through FIG. 26 are detailed flow charts showing the process steps of a part of the pulse wave amplitude processing program, which constitute measurement pattern forming means for elimination of noise and smoothing to secure the measurement patterns from the pulse wave amplitude data.
Figure 18:
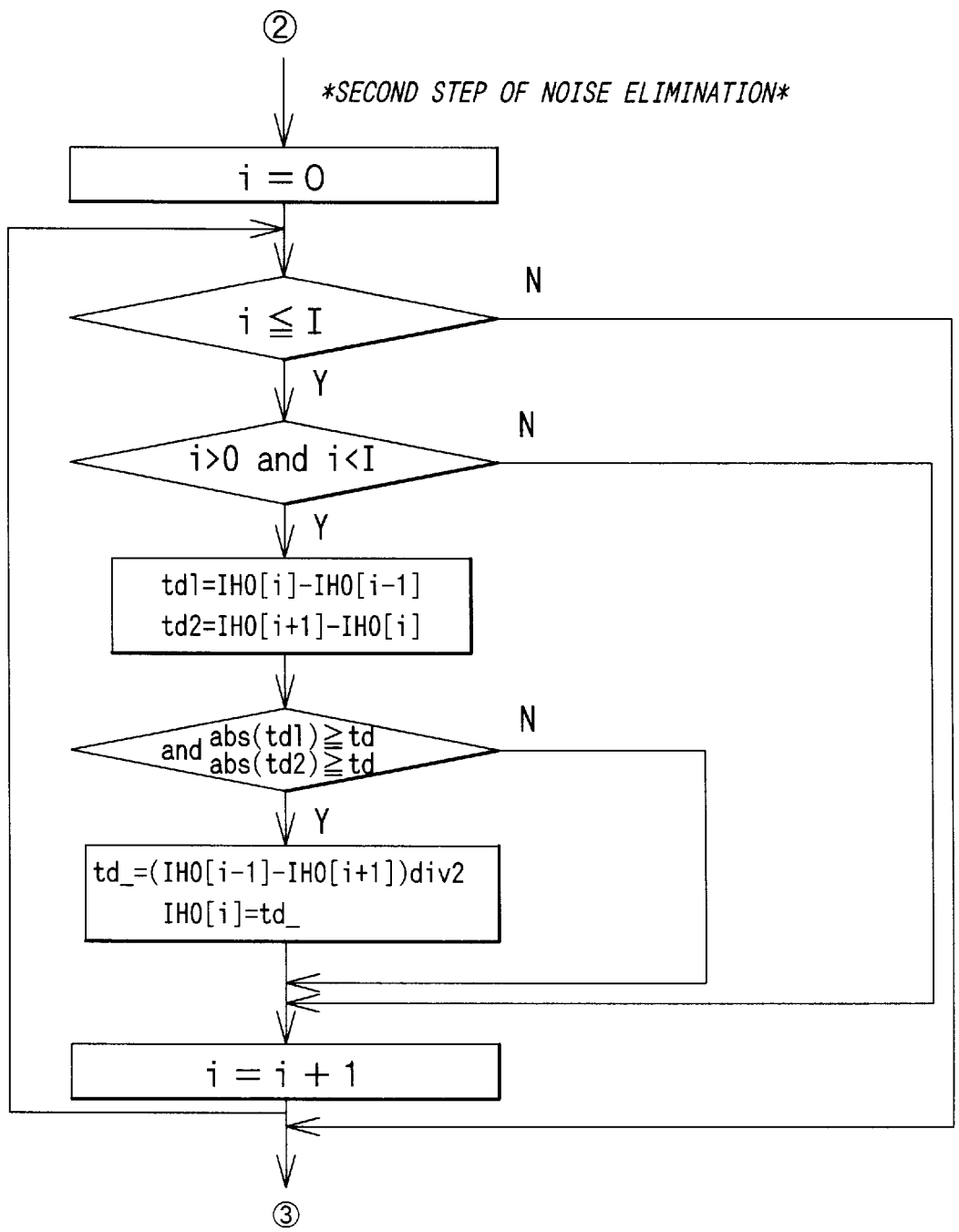
Figure 19:
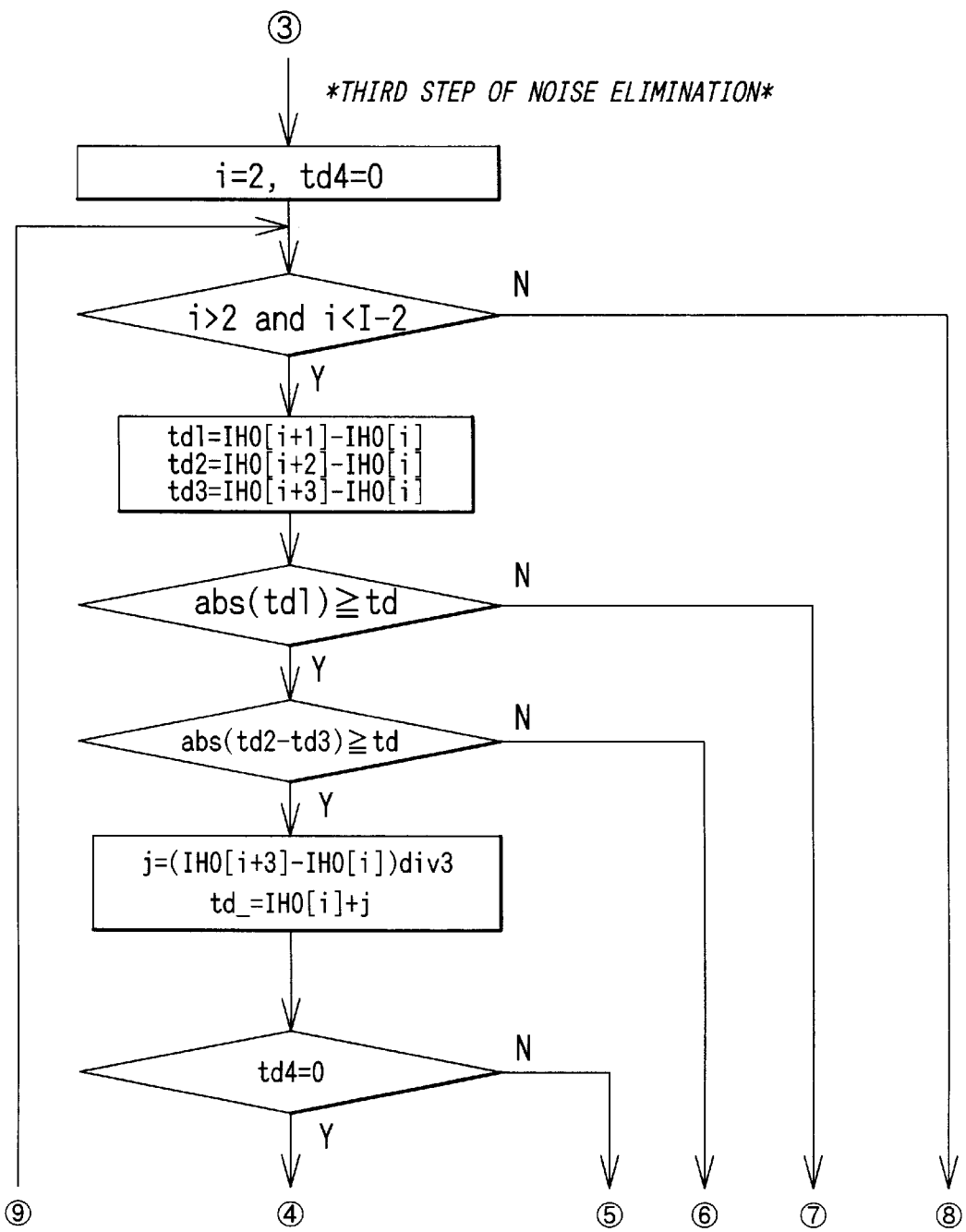
Figure 20:
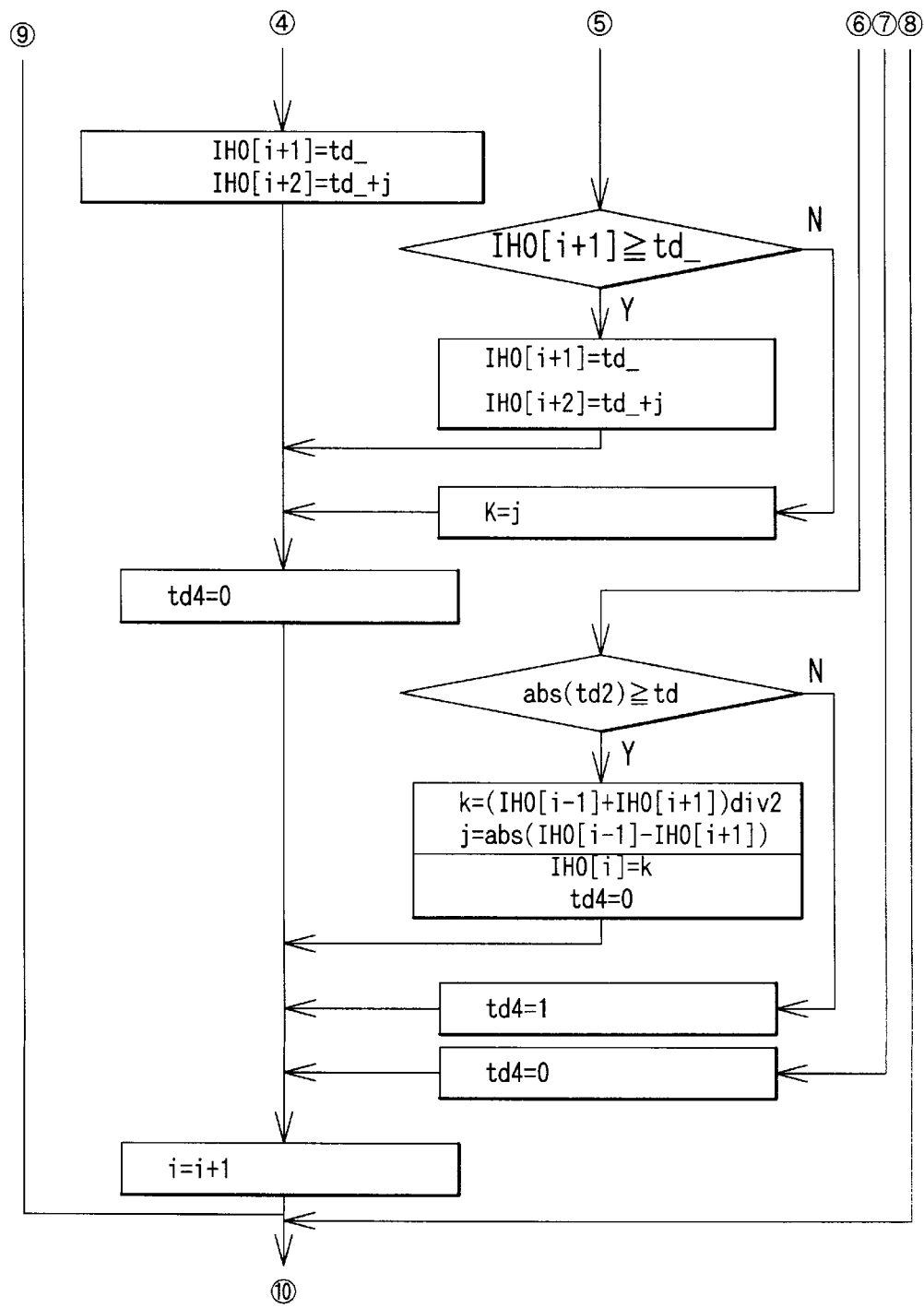

In the steps for eliminating noise, as shown in FIG. 17, firstly, the maximum fluctuation quantity td1 of the pulse wave amplitude value data PA[i] is obtained, thereby calculating the half value td=td½ of the maximum fluctuation quantity td1. Furthermore, the value of the pulse wave amplitude value data PA[i] is substituted in IH0[i]. In the subsequent steps, this IH0[i] is used. Next, as shown in FIG. 18, the differences between IH0[i] and the two adjacent (front and rear) data, that is, the difference between IH0[i] and IH0[i−1] is made td1 and the difference between IH0[i+1] and IH0[i] is made td2, whereby if both the absolute values of these td1 and td2 are larger than td, the half value of the difference between IH0[i−1] and IH0[i+1] is given to the value of IH0[i] as a correction. Furthermore, as shown in FIG. 19, the differences between IH0[i] and the adjacent subsequent three data are made td1, td2, and td3. Unless td1 is larger than td, no correction is carried out. If td1 is larger than td, the difference between td2 and td3 is compared with td, wherein if the difference between td2 and td3 is more than td, the values of IH0[i+1] and IH0[i+2] are respectively given, as a correction, to the values at the equally divided points wherein the difference between IH0[i] and IH0[i+3] is equally divided into three. However, this step is constructed so that whether or not such a process is carried out is judged, depending on the value of IH0[i+1] and the previously processed conditions as shown in FIG. 20. Furthermore, if the difference between td2 and td3 is less than td and the absolute value of td2 is more than td, the IH0[i] is corrected to the mean value of the two adjacent data values, IH0[I−1], IH0[i+1].

Next, as shown in FIG. 21, the half value td and quarter value td1 of the sum of the two adjacent values are obtained, wherein if IH0[i] is less than one-fourth of the sum of the two adjacent values and is more than three fourths thereof, the value of IH0[i] is corrected to td. Furthermore, as shown in FIG. 22, the half value td and one-sixth value td1 of the sum of the two adjacent values are obtained, wherein if IH0[i] is less than one-third of the sum of the two adjacent values or is more than two-thirds thereof, the value of IH0[i] is corrected to td.

Next, as shown in FIG. 23, weighted avarage of IH0[i] and the two adjacent data is computed by use of td and smoothed data IH1[i] are obtained by use of the weighted average, and they are stored as IH1[i] data.

The maximum value of the value td is stored as Hetop. Subsequently, an appointed numeral ( 1000000) is divided by Hetop in order to calculate the normalization multiplication ratio Mgn.

Next, as shown in FIG. 24, the data IH1 [i] of the pulse wave amplitude normalized as above is multiplied by Mgn to be normalized. That is, the maximum value of the pulse wave data is adjusted to become an appointed number (10000).

Next, the pulse wave amplitude data IH1 [i] normalized above and the pulse wave time data IH2 [i] (=PT[i]) are used for getting an expression by a spline curve. The fluctuation values of pulse wave amplitude expressed by these spline curves are re-defined. That is, first, the spline curve showing the fluctuated values of pulse wave amplitude is obtained by way of that the data of IH1[i] and IH2[i ] are substituted in a spline function SP(x) which forms a spline curve, and then the data SDP[m] (m=1,2,3, . . . M) corresponding to 200 pulse wave amplitude values (M=200) along the spline curve are obtained from the entire data range at an equal interval of a series of times SDT[m] which show the time corresponding to the data of data number m. The data SDP[m] is shown by graph (e) of FIG. 4. A smoothing step is carried out again for the data SDP[m] of the pulse wave amplitude as shown in FIG. 25, and as shown in FIG. 26, a normalization step is performed again. As described above, a series of normalization amplitude data SPP[m] which express a measurement pattern of the normalized pulse wave amplitude is formed. Furthermore, the series of normalization interval data SDT[m] are already normalized, and the shape of the measurement pattern is expressed by these series of normalization amplitude data SPP[m] and normalization interval data SDT[m]. This measurement pattern is shown by graph (f) in FIG. 4. The maximum value of the amplitude value of the pulse wave amplitude measurement pattern which is noise-eliminated, smoothed and normalized has become 1000.

Figure 27:
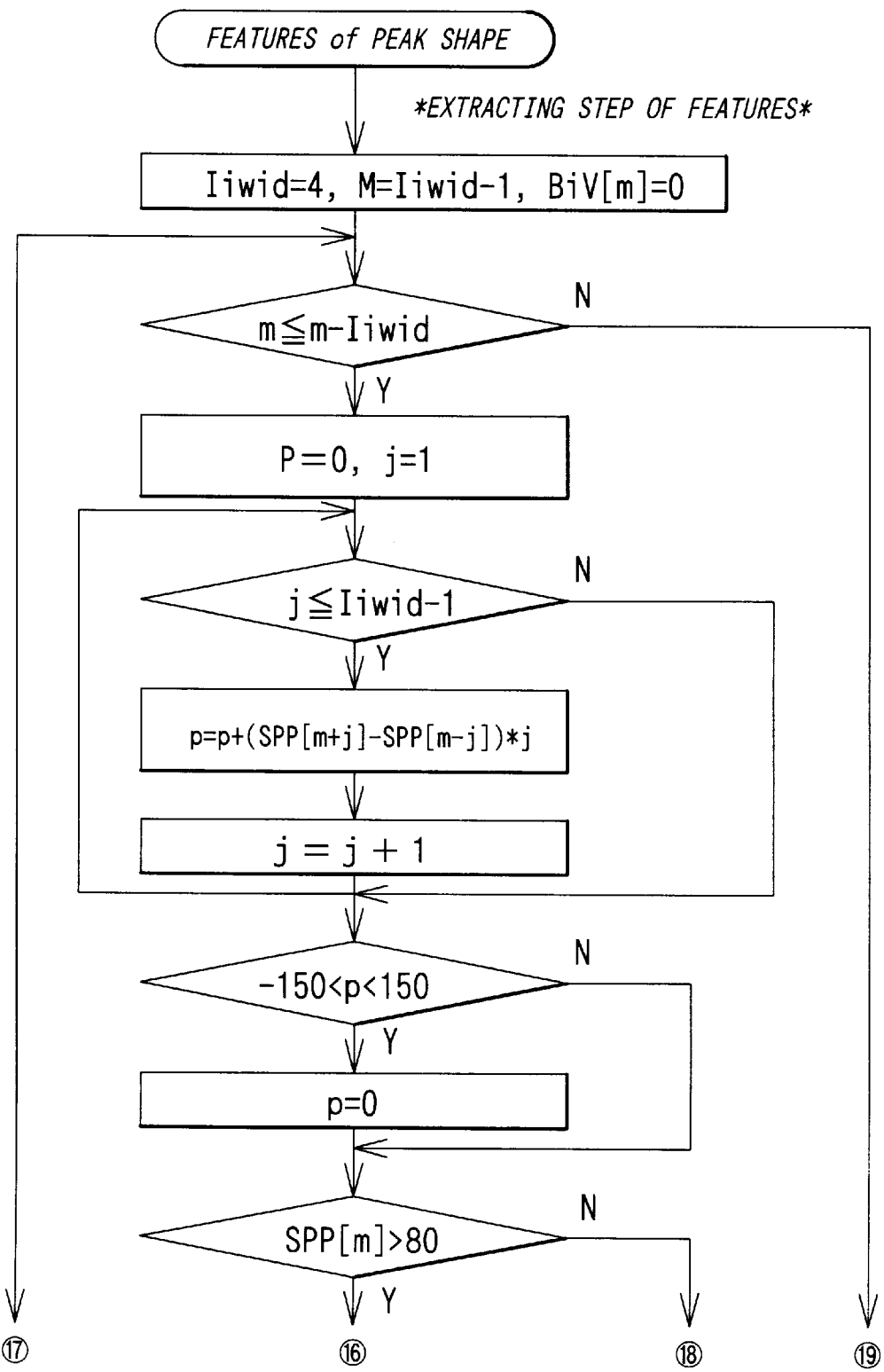
FIG. 27 through FIG. 31 are detailed flow charts showing the process steps of a part of the pulse wave amplitude processing program, which constitute a part of the feature extracting means for extracting the features pertaining to the shapes of the measurement patterns.
Figure 28:
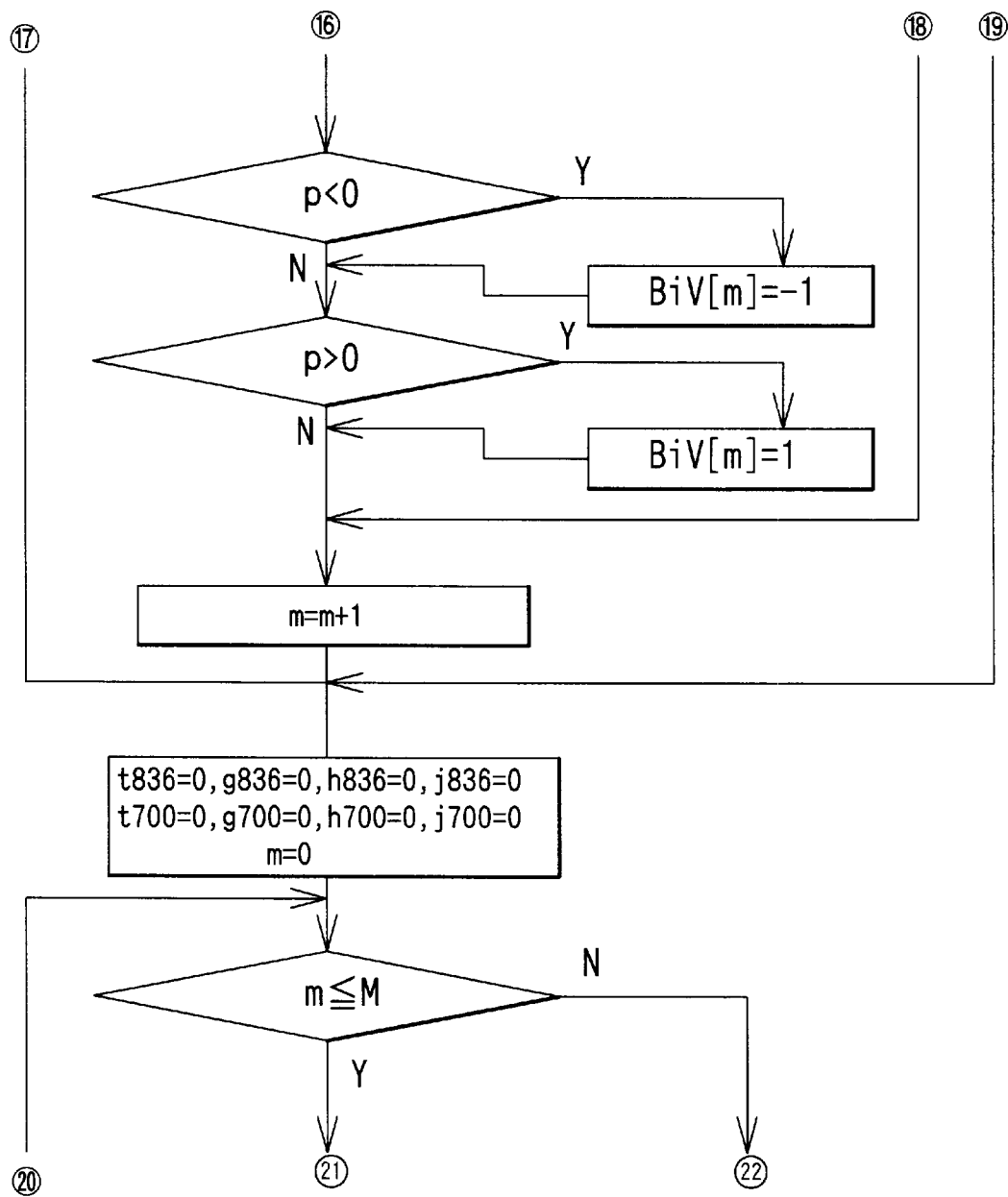
Figure 29:
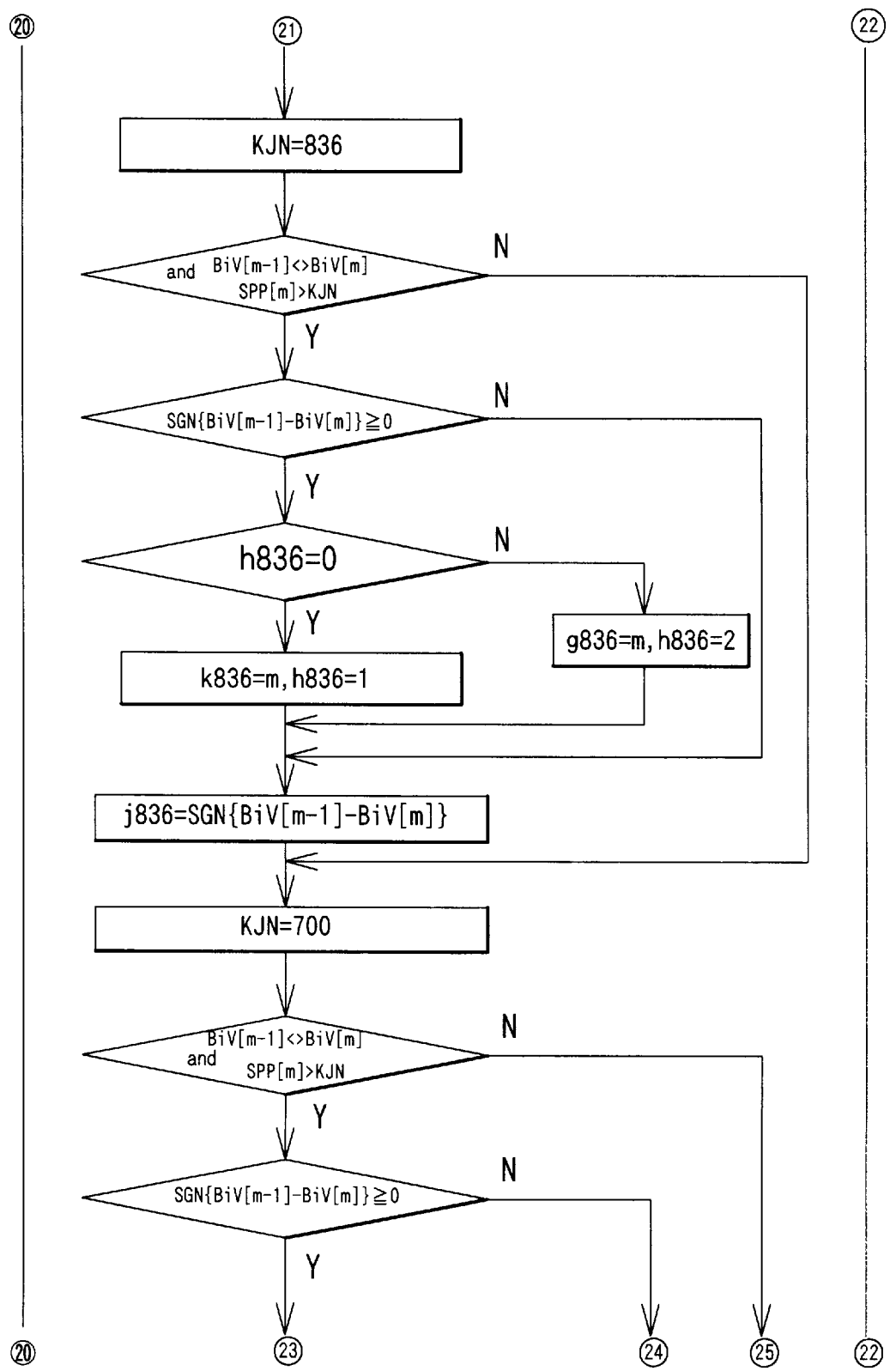
Figure 30:
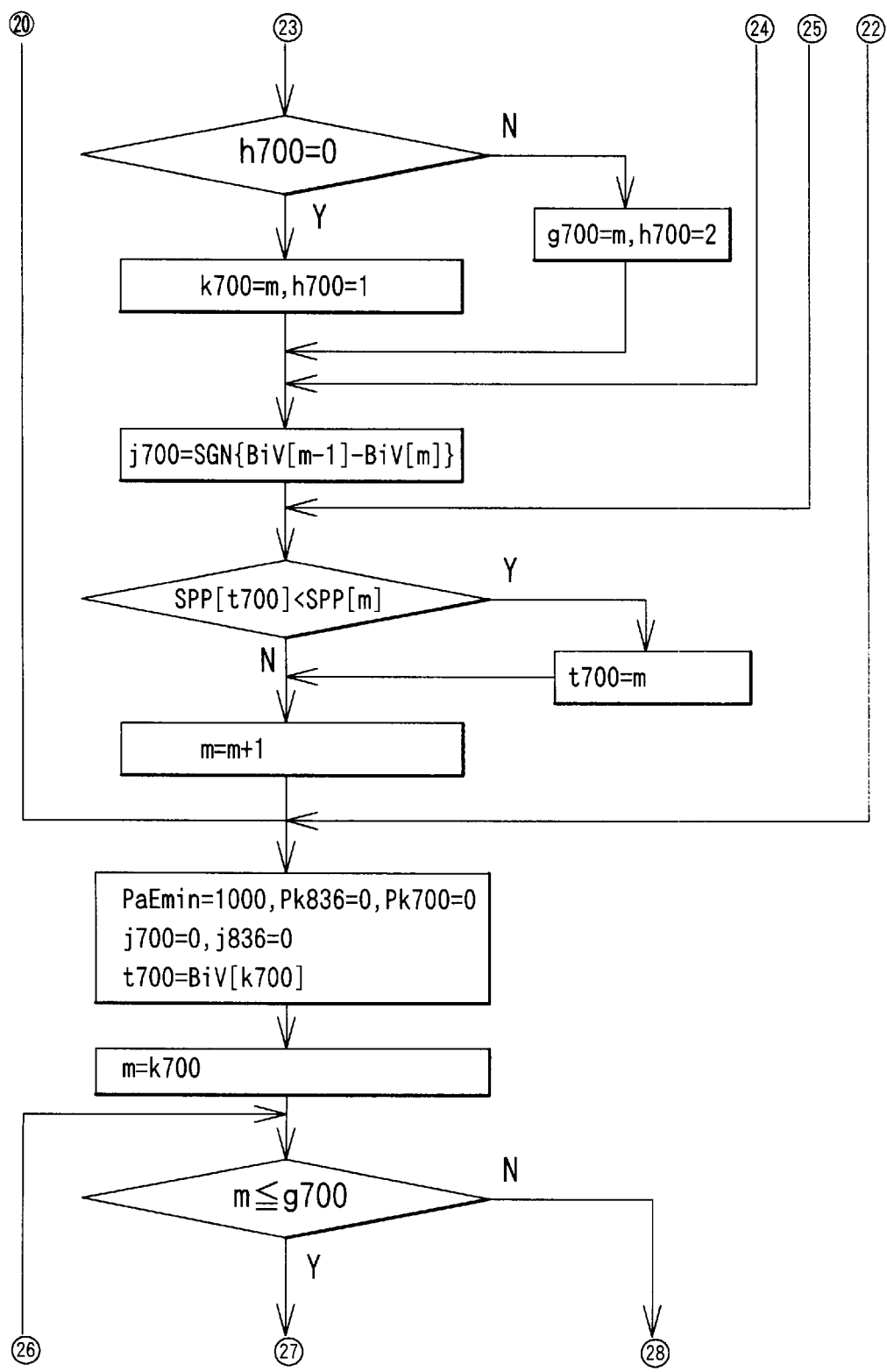

Next, as shown in FIG. 27, the difference between the values apart from each other by j (j=1 to 3) before and after the amplitude value data SPP[m] of this measurement pattern is added by the weight of j, and as shown in FIG. 28, the value (any one of −1,0, +1 is taken) of BiV[m] corresponding to the SPP[m] is obtained by the sign of the sum p. The value of this Biv[m] is determined to be a value corresponding to the sign of the sum p where the absolute value of the sum p exceeds 150, in the state where the Biv[m] is made 0 in a case where the value of SPP[m] is 80 or less for elimination of noise, and it is made 0 when the absolute value of the sum p is less than 150. That is, since the sum p will take a value responsive to the fluctuation ratio of SPP[m], the value Biv[m] becomes +1 in a case where the sum p exceeds 150 and the fluctuation ratio of SPP[m] is positive, and becomes −1 in a case where the sum p is less than −150 and the fluctuation ratio of the SPP[m] is negative.

Next, as described at the lower part of FIG. 28, the parameters k836, g836 obtained with respect to the high reference range which takes a value higher than the value equivalent to 83.6% of the maximum value 1000 of the measurement pattern SPP[m], that is, 836, and parameters k700, g700 obtained with respect to the low reference range which takes a value lower than the value of 70% of the maximum thereof, that is, 700, are introduced. These parameters are calculated by the process shown in FIG. 29 and FIG. 30. The high reference range means a range from the data number at which SPP[m] becomes 836 or more for the first time to the data number immediately before the data number at which SPP[m] goes below 836, and the lower reference range means a range from the data number at which SPP[m] becomes 700 or more for the first time to the data number immediately before the data number at which SPP[m] goes below 700.

Figure 35:
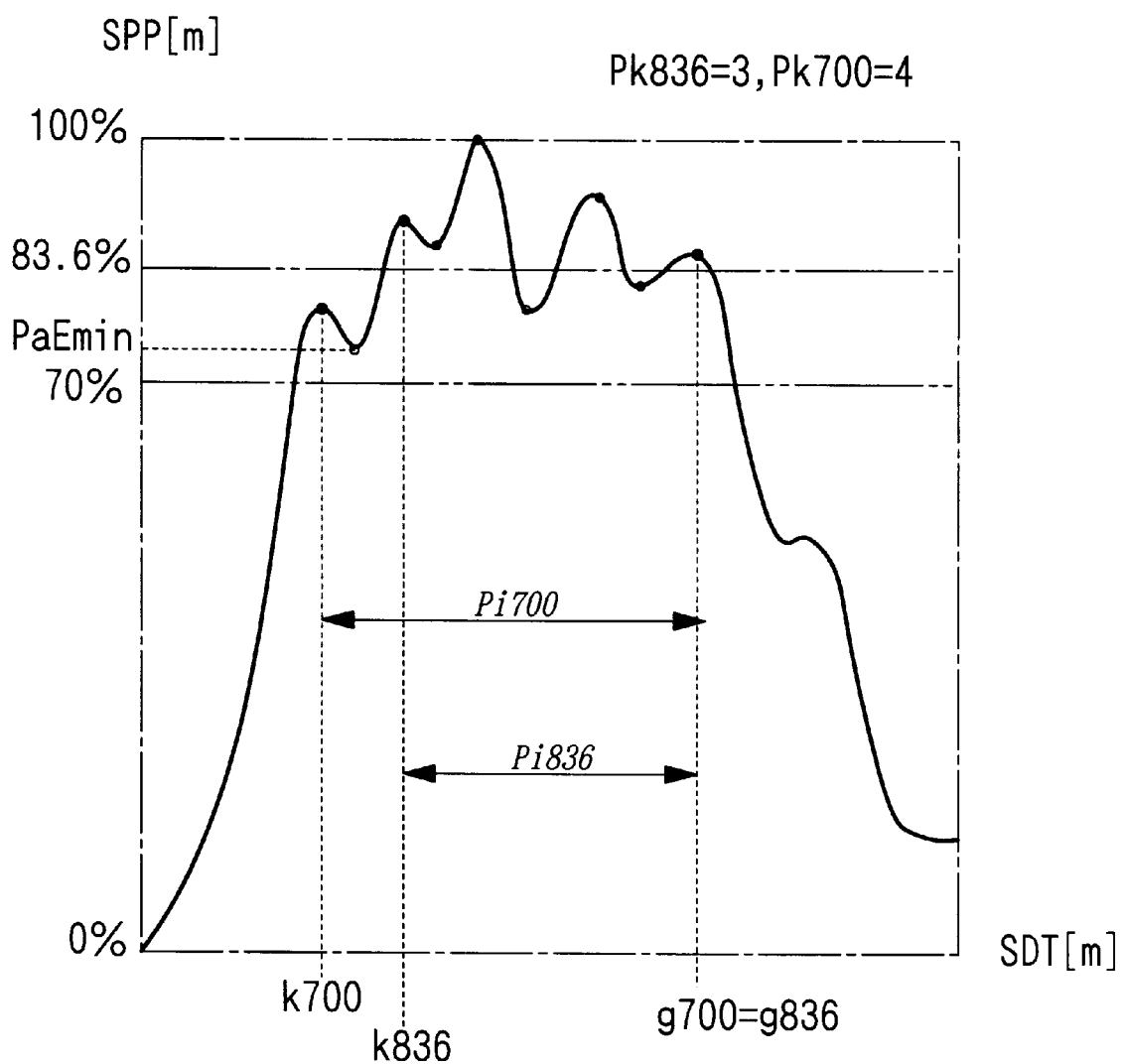
FIG. 35 is an explanatory view for explaining the meanings of variables(parameters) showing the features of the pattern shapes extracted in the pulse wave amplitude processing program.

Said k836 shows the data number of the first peak position (maximum value point) in the high reference range, and g836 means the data number of the final peak position in the high reference range. Furthermore, k700 shows the data number of the first peak position (the maximum value point) in the low reference range, and g700 means the data number of the final peak position in the low reference range, wherein the range from k836 to g836 is regarded as the high reference peak domain, and the range from k700 to g700 is made the low reference peak domain. These parameters are shown in FIG. 35.

Figure 31:
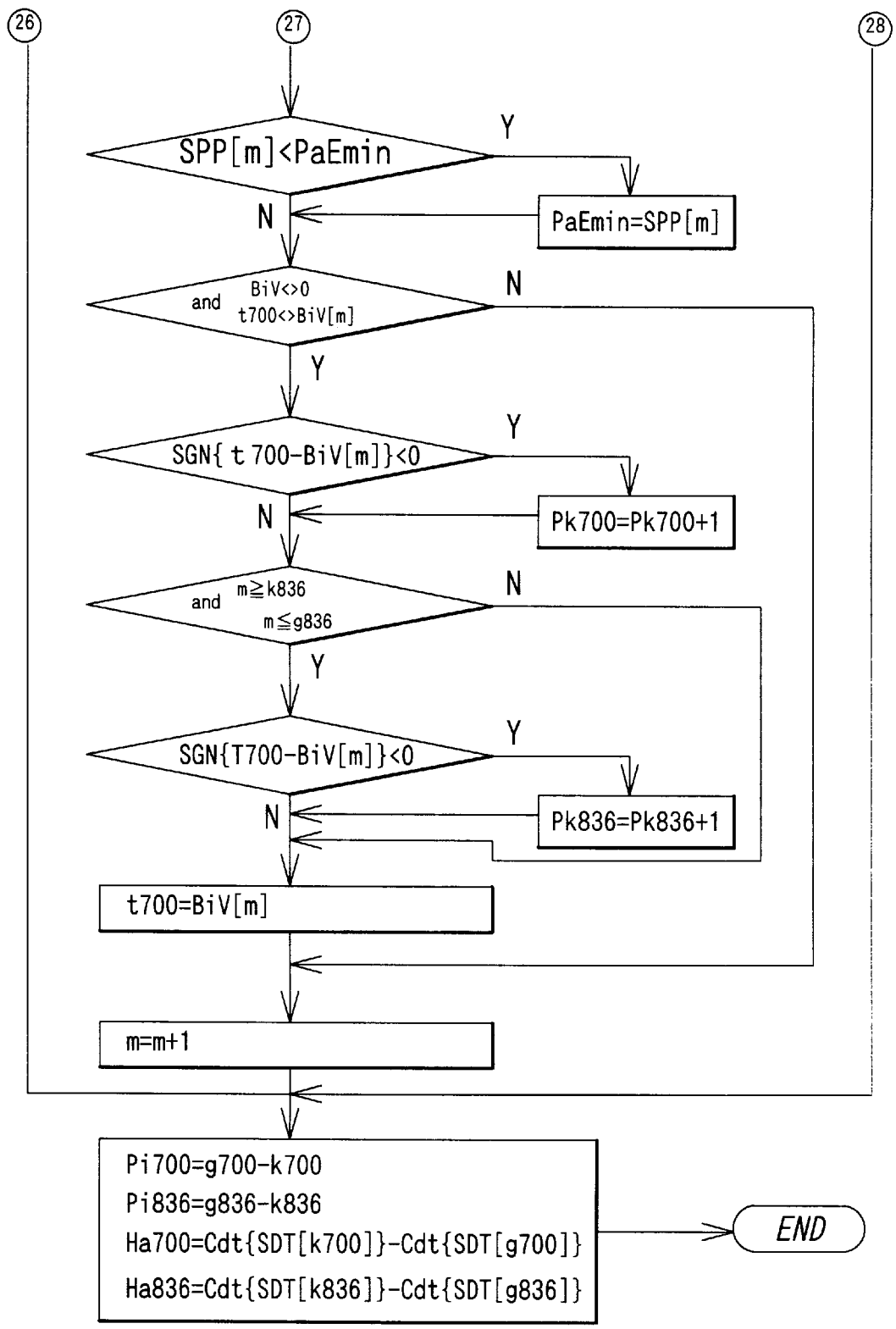

Next, as shown in FIG. 31, PaEmin showing the minimum value of SPP[m] in the low reference peak domain, the high reference minimum value number Pk836 showing the number of the minimum value points in the high reference peak domain, and the low reference minimum value number Pk700 showing the number of the minimum value points in the low reference peak domain are obtained. These parameters are also shown in FIG. 35.

Finally, the low reference peak width Pi700 showing the width from the first peak position (maximum value point) in the low reference range to the final peak position (maximum value point) and the high reference peak width Pi836 showing the width from the first peak position (maximum value point) in the high reference range to the final peak position (maximum value point) are obtained. Furthermore, the exhaust pressure difference Ha700 and Ha836 are calculated, which show the fluctuation quantities of the cuff pressure in the elapse time corresponding to these low reference peak width Pi700 and high reference peak width Pi836.

The meaning of the respective variables (parameters) showing the features (characteristic points) of the measurement patterns described above are described in FIG. 35. However, the measurement pattern shown in FIG. 35 is hypothetically formed for explaining the above variables which express the features.

Figure 32:
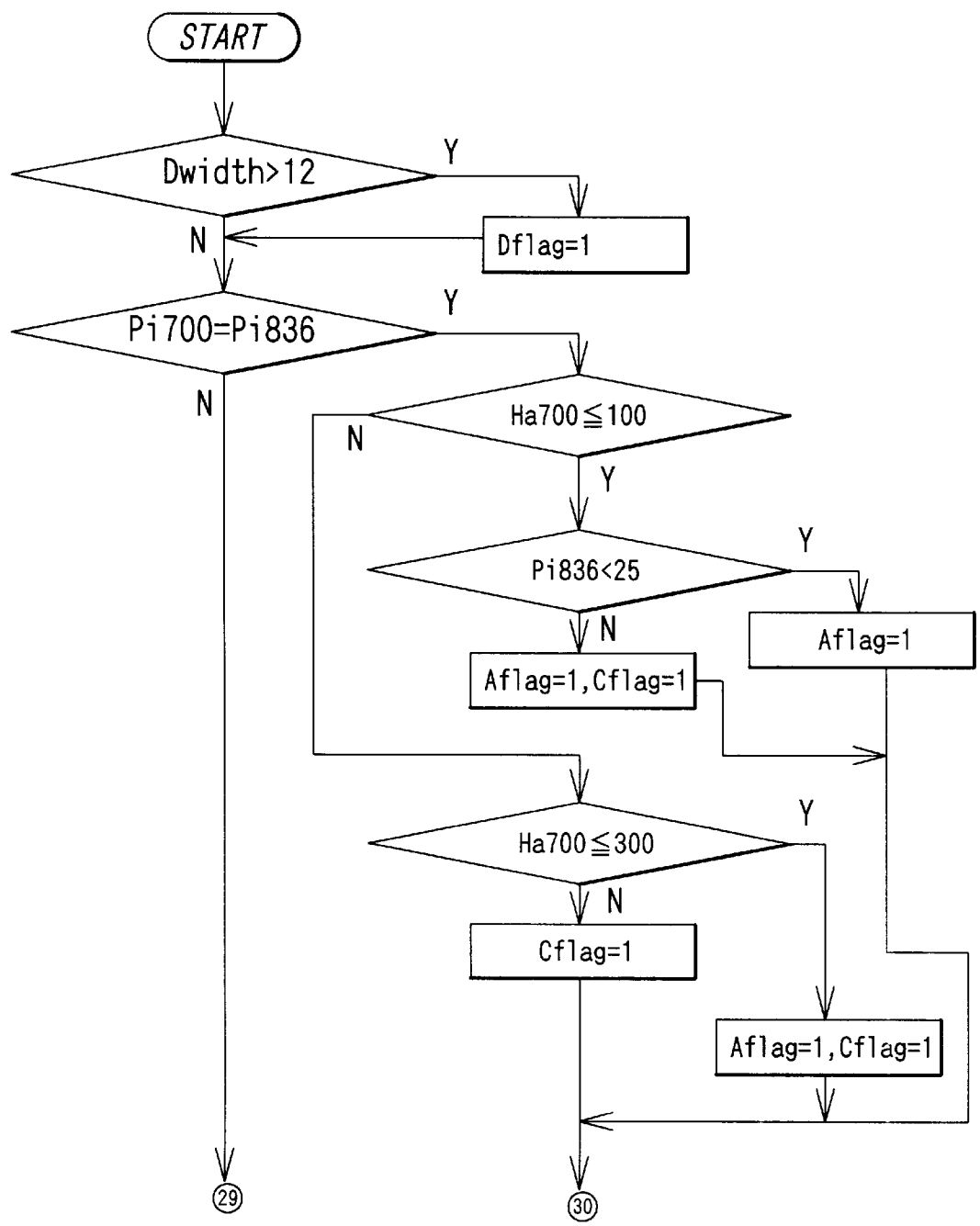
FIG. 32 through FIG. 34 are detailed flow charts showing the process steps of a part of the pulse wave amplitude processing program, which constitute a comparison judging means of apart of the pattern judging means.
Figure 33:
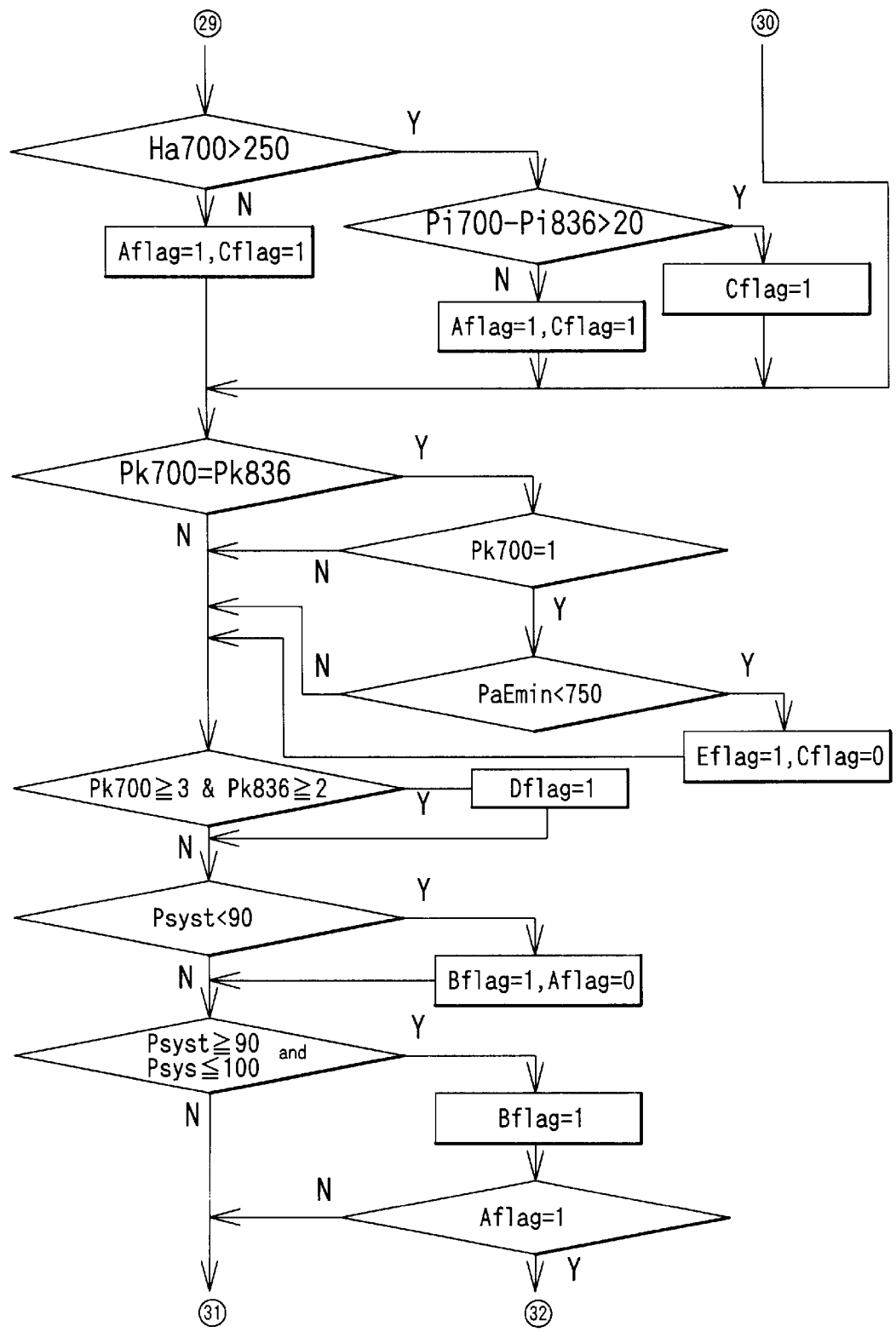
Figure 34:
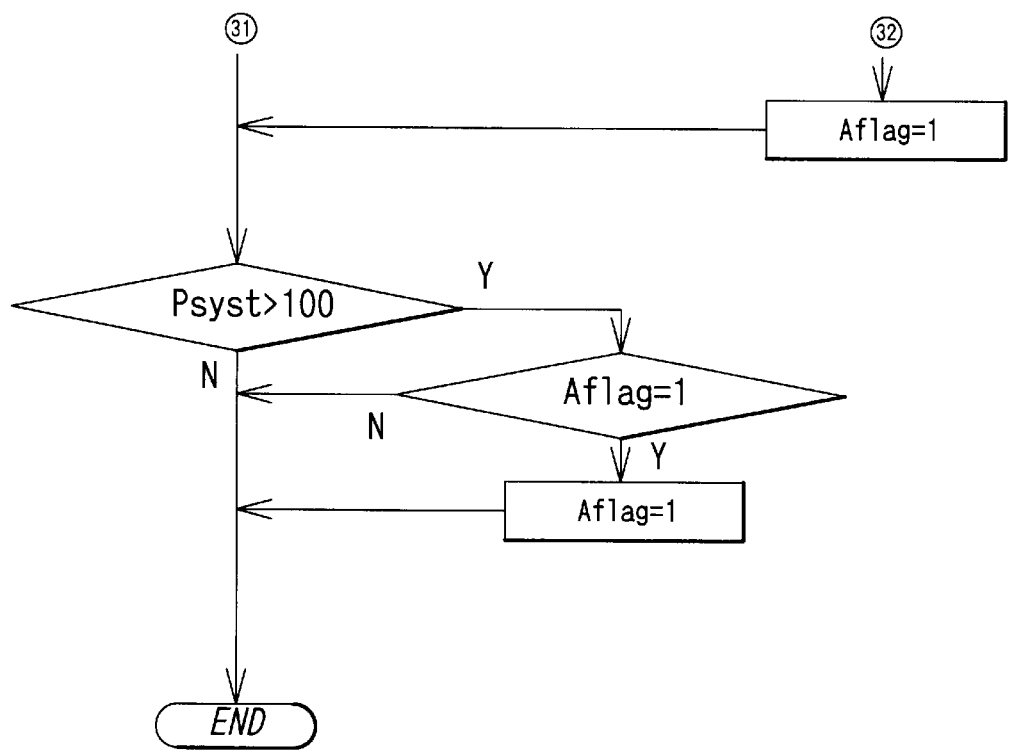

Finally, based on the features of the measurement patterns extracted as shown above, a pattern judgement is carried out with respect to the measurement pattern. The judgement sequences are shown in FIG. 32 through FIG. 34. The standards to be used for this judgement procedure are as follows;

(1) If the value Dwidth which is difference between the minimum value and the maximum value of the measurement pattern is more than 12, it is judged that the time irregularity of the measurement pattern is large and that the measurement pattern belongs to the reference pattern group D. The unit of this Dwidth is the measurement interval 50 milliseconds of the cuff pressure, and Dwidth=12 corresponds to 600 milliseconds.

(2) When the exhaust pressure difference Ha700 is 100 or less and Pi836 is less than 25 in a case where the low reference peak width Pi700 is equal to the high reference peak width Pi836, it is judged that the measurement pattern belongs to the reference pattern group A. In a case of Pi700=Pi836, it is judged that the peak shape is considerably simply mountain-like or trapezoidal. Furthermore, in a case where the value of Pi700=Pi836 is less than 25 and the exhaust pressure difference is 100 or less, it means that the width of the peak domain is small, and the peak shape is not trapezoidal but mountain-like.

(3) When the exhaust pressure difference Ha700 is less than 100 and Pi836 is 25 or more in a case where the low reference peak width Pi700 is equal to the high reference peak width Pi836, it is judged that the measurement pattern belongs to the reference pattern group A and reference pattern group C. In this case, the peak width is considerably narrow at a height of 70% of the maximum value of the pulse wave amplitude, and the peak width is not made narrow even at a height of 83.5% thereof. Therefore, it is judged that the measurement pattern belongs to both the reference pattern group A and reference pattern group C as there being a possibility that the pattern shape is trapezoidal.

(4) When the exhaust pressure difference Ha700 exceeds 100 but is 300 or less in a case where the low reference peak width Pi700 is equal to the high reference peak width Pi836, it is judged that the measurement pattern belongs to the reference pattern group A and reference pattern group C. In this case, since the peak width at a height of 70% of the maximum amplitude value is comparatively wide, it is judged that the measurement pattern belongs to the reference pattern group A and reference pattern group C.

(5) When the exhaust pressure difference Ha700 exceeds 300 in a case where the low reference peak width Pi700 is equal to the high reference peak width Pi836, it is judged that the measurement pattern belongs to the reference pattern group C. In this case, since the peak width at a height of 70% of the maximum amplitude value is considerably wide, it is judged that the measurement pattern belongs to the reference pattern group C.

(6) When the exhaust pressure difference Ha700 is 250 or less in a case where the low reference peak width Pi700 is different from the high reference peak width Pi837, it is judged that the pulse interval belongs to the reference pattern width A and reference pattern group C. Since Pi700 is different from Pi836, a peak position which is lower than 83.6% of the maximum amplitude value and is higher than 70% of the maximum amplitude value exists in the pattern shape, whereby since it is presumed that there is disorder in the peak shape although the peak domain width is comparatively narrow, it is judged that there is a possibility f or the measurement pattern to belong to the reference pattern group C in addition to the reference pattern group A.

(7) When the exhaust pressure difference Ha700 exceeds 250 in a case where the low reference peak width Pi700 is different from the high reference peak value Pi836, and further the difference between the low reference peak width Pi700 and the high reference peak width Pi836 is 20 or less, it is judged that the measurement pattern belongs to the pattern A and pattern C. In this case, since there is little disorder although the width of the peak domain is comparatively wide, it is judged that the measurement pattern belongs to the reference pattern group A and reference pattern group C.

(8) When the exhaust pressure difference Ha700 exceeds 250 in a case where the low reference peak width Pi700 is different from the high peak reference value width Pi836, and the difference between the low reference peak value Pi700 and the high reference peak width Pi836 exceeds 20, it is judged that the measurement pattern belongs to the reference pattern group C. In this case, since the width of the peak domain is wide and the disorder of the peak shape is large, it is judged that there is almost no possibility for the measurement pattern to belong to the reference pattern group A.

(9) When the low reference minimum value number Pk700 is equal to the high reference minimum value number Pk836 and the value is 1, and the minimum value PaEmin in the low reference peak width is less 750, it is judged that the measurement pattern belongs to the reference pattern group E. In this case, the minimum value point (reversed peak) which shows a considerably low amplitude value exists in the peak domain. In this case, since there is no possibility for the measurement pattern to belong to the reference pattern group C, the flag of the group C is made 0.

(10) In a case where the low reference minimum value number Pk700 is 3 or more and the high reference minimum value number Pk836 is 2 or more, it is judged that the measurement pattern belongs to the reference pattern group D. In this case, since the shape of the peak domain of the measurement pattern is considerably disordered, for example, even though said Dwidth is small, there is a high possibility that the measurement pattern belongs to the reference pattern group D.

(11) when in the abovementioned judgement standards (2), (3), (4), (6) and (7), it is already judged that the measurement pattern belongs to the reference pattern group A and furthermore, in a case where the maximum blood pressure value Psyst exceeds 100, it is now judged again that the measurement pattern belongs to the reference pattern group A. In a case where the maximum blood pressure is less than 90 it is judged that the measurement pattern belongs to the reference pattern group B and don't belong to the reference pattern group A, and in a case where the maximum blood pressure value is 90 or more but 100 or less, it is judged that the measurement pattern belongs to the reference pattern group B.

The results of judgement in a case where a system including a pattern judgement means constructed as above is actually adapted to a patient are evaluated. In this evaluation, actual measurements are carried out on a subject group consisting of 417 people of various ages, some of whom seem to be fine and the others of whom have various kinds of abnormalities, which including 170 persons who are diagnosed to be fine. The results obtained by the system are compared with the results obtained by manual process in compliance with the symptoms described in FIG. 7, which are classified into any one of the five patterns on the basis of the diagnosis performed on the same subject group by a medical doctor in accordance with a general discrimination method. The experimental data are shown in Table I below.

TABLE I

| | | X: Classification by medical Dr. | | | | | |
|---|---|---|---|---|---|---|---|
| | | A | B | C | D | E | Y |
| Y: | A | 112 | 0 | 55 | 3 | 0 | 170 |
| Automatic | B | 0 | 15 | 1 | 0 | 1 | 15 |
| Classifi- | C | 24 | 1 | 140 | 3 | 7 | 175 |
| cation | D | 4 | 0 | 4 | 26 | 1 | 35 |
| | E | 1 | 0 | 8 | 4 | 9 | 22 |
| | X | 141 | 16 | 207 | 36 | 17 | 417 |

Table I above shows a correlation between the diagnosis results (X) made by a medical doctor and the automatic judgments (Y) performed by this system. The evaluation is carried out in accordance with the three parameters shown by the expression described below, wherein the number of cases where both X and Y belong to a specified reference pattern group (that is, number of cases where the positive results are coincident with each other) is made "a", the number of cases where although it is judged that X does not belong to the reference pattern group, Y is judged to belong to the reference pattern group, is made "b", the number of cases where although X belongs to the reference pattern group, Y is not judged to belong to the reference pattern group is made "c" and the number of cases where both X and Y do not belong to the reference pattern group (that is, number of cases where the negative results are coincident with each other) is made "d":

Sensitivity $(\%) = a/(a+c) \times 100$

Specificity $(\%) = d/(b+d) \times 100$

Coincidence ratio $= (a+d)/(a+b+c+d) \times 100$

The results are shown in Table II below.

TABLE II

| | Classification pattern | | | | |
|---|---|---|---|---|---|
| | A | B | C | D | E |
| Sensetivity | 79.4 | 93.8 | 67.6 | 72.2 | 52.9 |
| Specificity | 79.0 | 100.0 | 83.3 | 97.6 | 96.8 |
| Agreement rate | 79.1 | 99.8 | 75.5 | 95.4 | 95.0 |

As shown in Tables I and II, the automatic judgement of measurement patterns by this system is provided with a statistical correlation for the diagnosis results made by a medical doctor, and the sensitivity, specificity and coincidence ratio between the automatic judgement and the diagnosis result by a medical doctor are high.

With this system constructed as described above, it is possible to know the states of the cardiovascular system, which are not able to be grasped with only the blood pressure values and pulse rate, with only the operations which are similar to those of the conventional blood pressure measurement. Although the measurement pattern of the pulse wave amplitude itself includes much information, it is possible with this system to judge to which one or more reference pattern groups A, B, C, D, or E the measurement pattern belong. The diagnosis of measurement pattern is not performed, but a judgement of to which one or more groups the pattern shape of the measurement pattern belongs is performed. However, since the features of the reference pattern groups established in advance is set so as to show a blood circulation corresponding to the states of cardiovascular system on the basis of the medical ground as described above, the judgement results will be provided with high medical value. Furthermore, the judgement made by this system is to give the objective index to a diagnosis made by a medical doctor and becomes a great help to perform a uniform and repeatable diagnosis.

Although five reference pattern groups are prepared in this system, the number of these reference pattern groups is not limited to five. In a case where a specially detailed judgement is performed for a plurality of medical symptoms, the number of necessary reference pattern groups will be increased, and in a case where there are some pattern shapes which are not necessarily important, the number of necessary reference pattern groups will be decreased.

Still furthermore, in this system, there may be a case where it is judged that the measurement pattern of pulse wave amplitude belongs to more than one group of the five reference pattern groups. In this case, the measurement pattern results from the cardiovascular conditions corresponding to more than one reference pattern group, and there is a case where plural symptoms concurrently occur, or a case where merely the inferiority of the measurement state may influence the measurement pattern shape. Still furthermore, there is a case where the symptoms of the patient are changing from a state which causes a certain reference pattern group to another state which causes another reference pattern group. For example, in a case where the measurement pattern is judged to belong to both the reference pattern groups A and C, there is a possibility for the patient to be in a state that his condition is changing from a healthy state to arteriosclerosis. In this system, there may be cases where a patient belongs to two reference pattern groups, three reference pattern groups or four reference pattern groups. As in the above, it has been verified through experiments that there exist people who belong to more than one reference pattern group. Generally, when judging the measurement pattern, although there is a possibility that the characteristic pattern shape of a reference pattern group is hidden by the characteristic pattern shape of the other reference pattern group, it is possible with this system to objectively find out the features of more than one reference pattern group even in such a case and to discover a latent disease through an accurate judgement.

Figure 36:
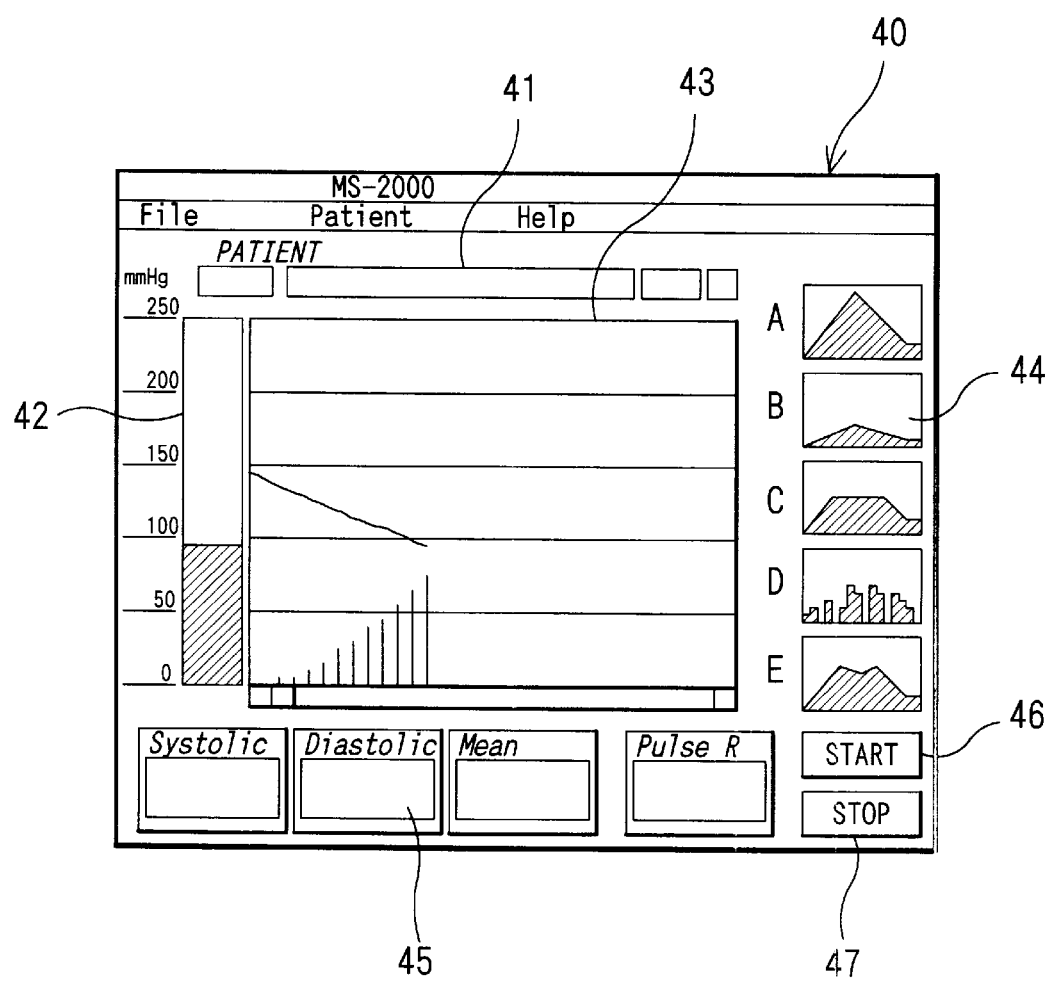
FIG. 36 is a view showing the embodiment of a display screen during a measurement.

FIG. 36 shows a main screen display 40 on the display 70 of a personal computer 60 while a measurement is being carried out through a blood pressure measurement adaptor 50. This screen display is the example of a case where Windows 3.1x is used as an operating system (OS). The display area 41 at the upper part of the window indicates patient information such as an identification number, name, classification number, data number, etc. of a patient registered in advance or newly inputted. The central part of the window shows a graph the ordinate of which shows a pressure value (mmHg) and the abscissa of which indicates time. There is a display area 42 along the ordinate of the graph, which displays the cuff pressure by a stripe whose length may change, and at the right hand side thereof there is a display area 43 where a linear graph showing the cuff pressure and a bar graph showing the pulse wave amplitude exist.

At the right end part of the window, a display area 44 is formed, which shows distinguishing characters (A through E) of the five reference pattern groups disposed vertically and typical pattern shapes belonging to the respective reference pattern groups. At the lower part of the window, a display area 45 is provided, which shows the systolic blood pressure, diastolic blood pressure, mean blood pressure and pulse rate. A start button 46 for commencing a measurement and a stop button 47 for stopping the measurement are provided at the right lower part of the window.

Figure 37:
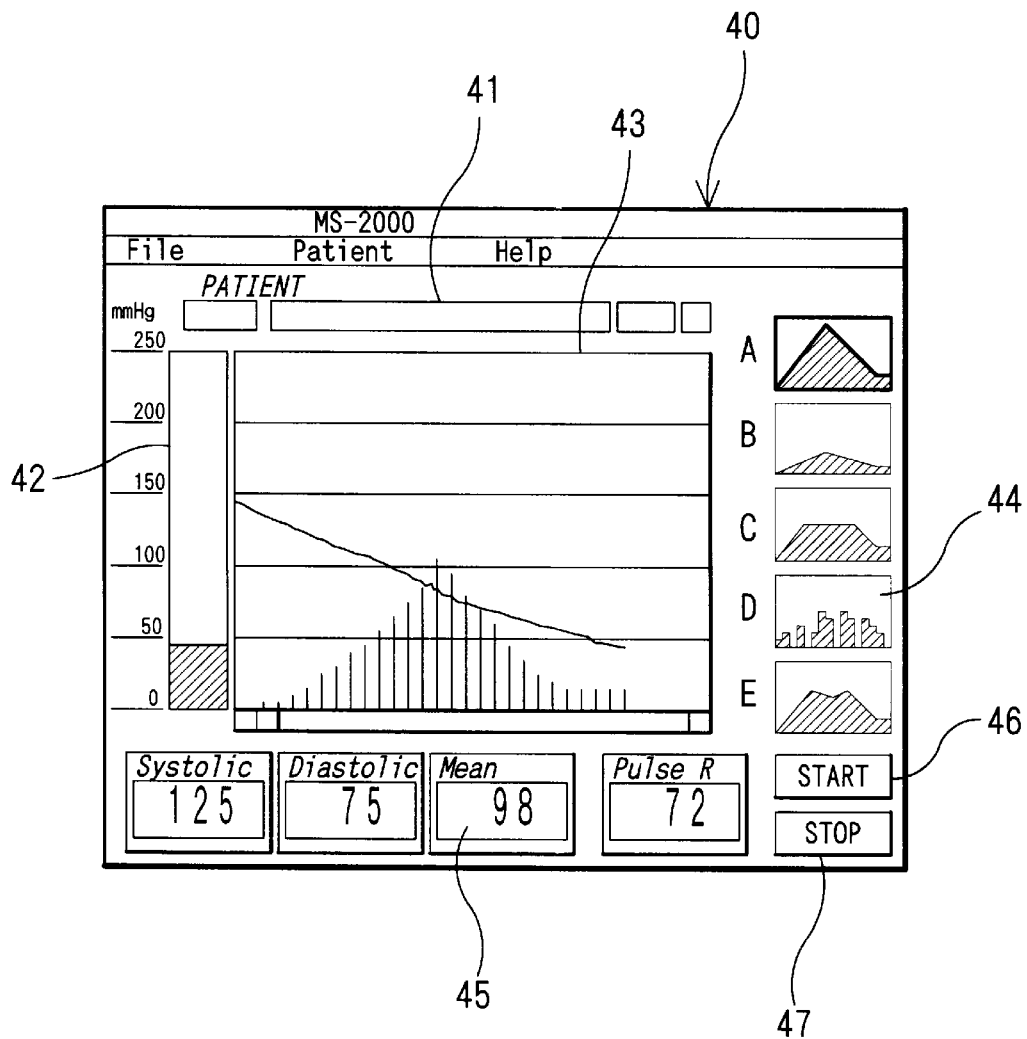
FIG. 37 is a view showing the embodiment of the display screen after the measurement is finished.

If the start button 46 is operated by an input operating device such as a mouse, the cuff 10 is compressed by the blood pressure measurement adaptor 50 connected to the personal computer 60 as described above, whereby a measurement is started. When the cuff pressure data C[n], pulse wave amplitude value data PA[i] and pulse wave time data PT[i] are transmitted from the blood pressure measurement adaptor 50 after the measurement is started, the graphs in the above display areas 42, 43 are displayed in real time, whereby as illustrated, graphic portion corresponding to the data are accumulatively displayed in accordance with the detection of the cuff pressure, the computation of the pulse wave amplitude and the receiving of these data. When the systolic blood pressure value Psyst, diastolic blood pressure Pdias, mean blood pressure value Pmean and pulse rate PR are transmitted from the blood pressure measurement adaptor 50 after the measurement is finished, the respective values are displayed on the display area 45 as shown in FIG. 37. Thereafter, as described above, when the measurement pattern of the pulse wave amplitude is formed and the result of judgement is obtained by executing a pattern judgement, only the pattern shape showing the reference pattern group to which the measurement pattern belongs is thickly displayed, and any other reference pattern groups to which the measurement pattern does not belong are thinly displayed.

Figure 38:
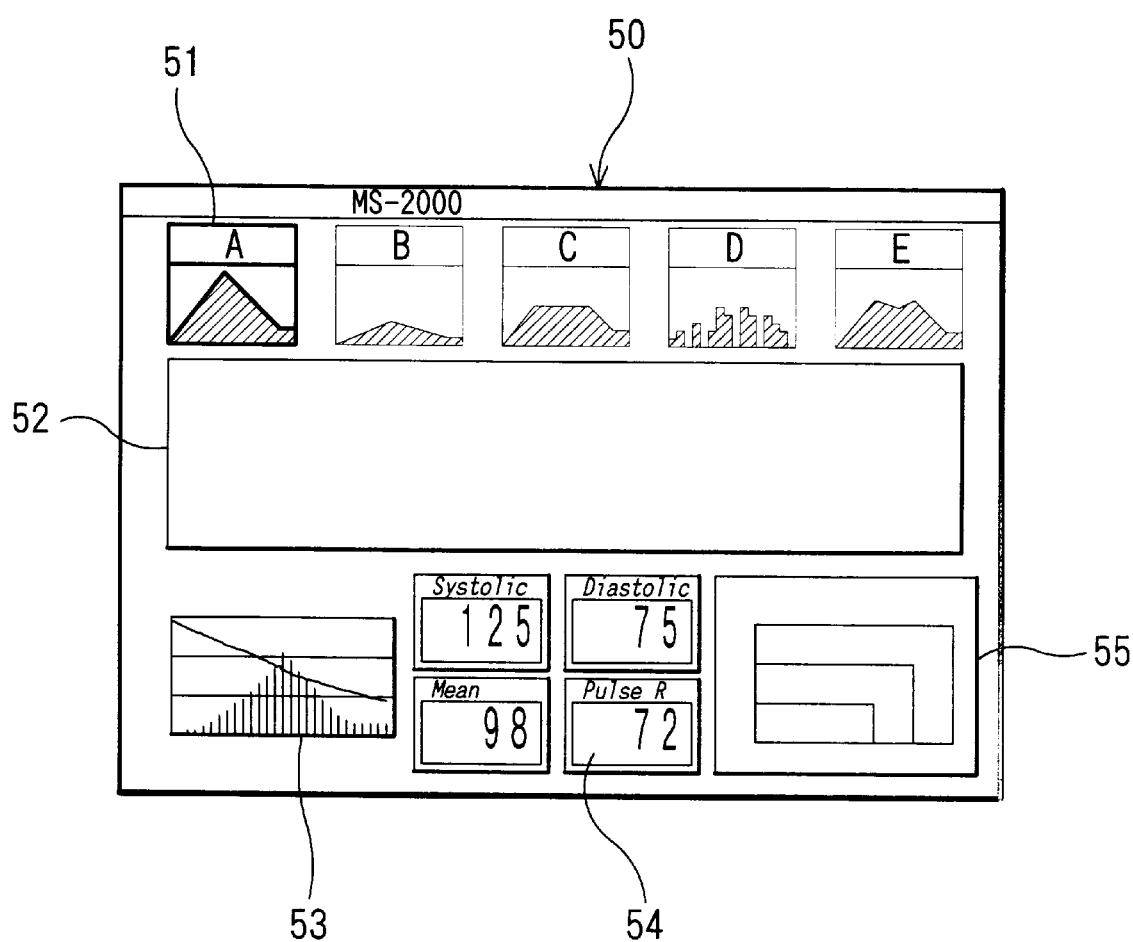
FIG. 38 is a view showing the embodiment of the display screen for explaining the reference pattern groups.

If any one of the pattern shapes in the display area 44 of this main screen display is selected with a mouse, a screen display 50 for explanation shown in FIG. 38 is devised to come out. On this explanation screen display, the characters and pattern shapes, which show the five reference pattern groups, are displayed in the display area 51 at the upper section of the window, a description of the reference pattern group selected in the display area 51 is devised to come out in the display area 52 which is below the display area 51. The default value selected in this case is for the reference pattern group to which the measurement pattern belongs as a judgement result, wherein it is possible to simultaneously select plural reference pattern groups in this display area 51, and a description in accordance with a combination of the reference pattern groups is caused to appear. The respective descriptions A–B, A–C, A–C–D, A–D, B–C, B–C, B–C–D, B–C–D–E, B–D, B–D–E, B–E, C–D, C–D–E, C–E, C–E, D–E are prepared as combinations of the reference pattern groups.

Display areas 53, 54, 55 are provided below the display area 52. The graphs showing the cuff pressure and pulse amplitude, which are identical to those displayed in the display area 43 of the main screen display 40 are displayed in the display area 53. The systolic blood pressure value, diastolic blood pressure value, mean blood pressure value and pulse rate which are identical to those displayed at the display area 45 of the main screen display 40 are displayed in the display area 54. A graph showing the divisions of ranges of hypertonia, normal and hypotension defined by WHO (World Health Organization) is displayed on the plane shown with the systolic blood pressure and diastolic blood pressure in the display area 55.

Figure 39:
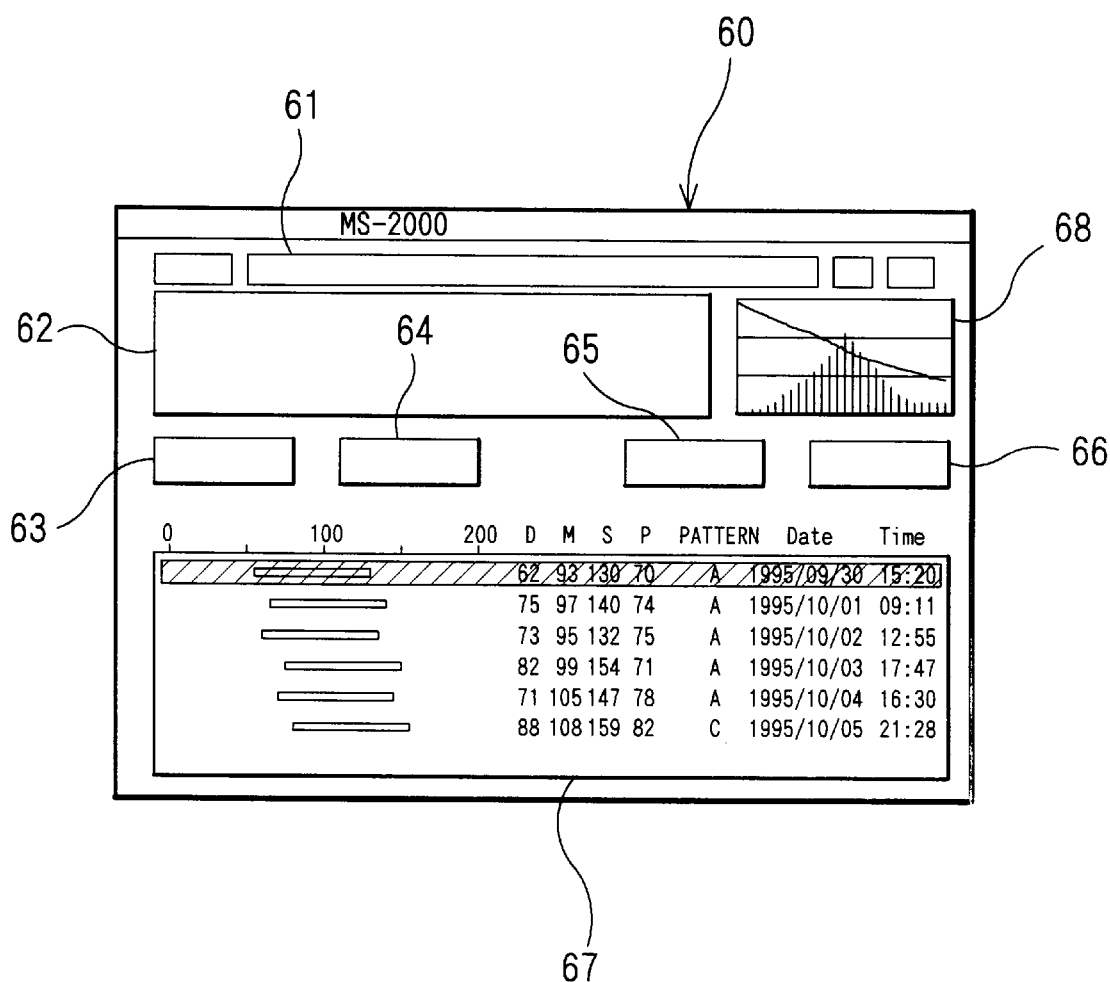
FIG. 39 is a view showing the embodiment of the display screen showing the past measurement data of a patient.

If "File" is selected on the main screen display 40, a menu appears, wherein if "Data Store" in this menu is selected, the measurement data (Systolic and diastolic blood pressure values, pulse rate, cuff pressure data, pulse wave amplitude data, judged reference pattern group(s)) are able to be stored together with the patient name, date of measurement and other descriptions. Furthermore, the data thus stored in memory are able to be loaded on the screen display by retrieval as necessary. When referring to the past measurement data of a patient, the corresponding menu is displayed by selecting "Patient", and "Select" is selected from this menu, a patient selection screen displayed. On this patient selection screen, it is possible to look at a list of patients whose measurement data are stored. If a specified patient is selected on the list, a patient history screen display 60 shown in FIG. 39 is displayed in order to display the past information of the selected patient.

On this patient history screen display 60, a patient name, etc. are displayed in the display area 61 at the upper section of the window, and a description recorded together with the measurement data selected in the display area 67 described later is displayed in the display area 62 below the display area 61. A deletion button 63 is to delete the measurement data selected in the area 67 described later, a list button 64 is to display a list of patient data, a call button 65 is to replace the data held at this moment with the data selected in the display area 67, and a close button is to close the patient history screen display 60. The past measurement data previously stored of the selected patient is displayed in the display area 67 together with the date of measurement, for example, in the sequence of measurement. The display area 68 displays a graph of the cuff pressure and pulse wave amplitude of the measurement data selected among a plurality of measurement data displayed in the display area 67.

In the patient history screen display 60, since it is possible to quickly confirm the past measurement data of a specified patient and to easily grasp the transition of the measurement data, the same is very convenient for a medical doctor to carry out a diagnosis of a patient. Especially, since it is possible to grasp not only the blood pressure values but also the shape of measurement patterns of pulse wave amplitude and transition of the judged reference pattern groups, it is possible to accurately diagnose the states of the cardiovascular system of a patient.

The entire disclosure of PCT International Patent Application No. PCT/JP94/00545 filed on Apr. 1, 1994 including specification, claims, drawings and summary are incorporated herein by reference in its entirety.

What is claimed is:

1. A cardiovascular system observation method which uses a computer processor for observing cardiovascular conditions of a patient based on pulse wave amplitude data, said data including information about pulse wave amplitude values and pulse wave intervals, and said data being obtained from pressure fluctuations which result from pulse waves which are issued from a body surface of said patient in a compressed state which changes between a higher pressure than a mean blood pressure of said patient and a lower pressure than said mean blood pressure, said cardiovascular system observation method comprising the steps of:

forming measurement patterns expressing transitions of said pulse wave amplitude values while pressure is gradually decreased or increased in said compressed state, said measurement patterns being formed by smoothing minute fluctuations of said pulse wave amplitude data and normalizing said pulse wave amplitude values and said pulse wave intervals of said pulse wave amplitude data;

extracting features of said measurement patterns by reference to a plurality of reference pattern groups corresponding to a plurality of cardiovascular conditions based on dynamic properties of blood vessels and cardiac output properties; and judging said measurement patterns to determine one or more of said reference pattern groups to which said measurement patterns belong by using said features obtained by said extracting features of said measurement patterns.

2. A cardiovascular system observation method as claimed in claim 1, including the steps of measurement patterns, an envelope for expressing said transitions of said pulse wave amplitude values is obtained by securing a curve adaptable to said pulse wave amplitude data.

3. A cardiovascular system observation method as claimed in claim 1 and further comprising:

displaying information about said measurement patterns on a display screen of a display means, said information including shapes of said measurement patterns being obtained by figuring or graphing said pulse wave amplitude data or said measurement patterns and also including indications of one or more of said reference pattern groups to which said measurement patterns belong.

4. A cardiovascular system observation method as claimed in claim 3, wherein in said displaying information about said measurement patterns, a graphic portion corresponding to said pulse wave amplitude data is accumulatively displayed by calculating or graphing said pulse wave amplitude data.

5. A cardiovascular system observation method as claimed in claim 1 and further comprising:

recording one or more sets of information in conjunction with said measurement patterns and also in conjunction with said one or more of said reference pattern groups to which said measurement patterns belong; and retrieving one or more sets of information and for displaying said sets on a display screen of said displaying means.

6. A cardiovascular system observation method as claimed in claim 1, in said step of extracting features of said measurement patterns irregularities of said pulse wave intervals, features for expressing peak shapes in said measurement patterns are extracted, and in said step of judging said measurement patterns, said irregularities of said pulse wave intervals and said features for expressing peak shapes are compared with a plurality of parameters established in advance based on said plurality of reference pattern groups and one or more of reference pattern groups to which said measurement patterns belong are determined in accordance with the results of said comparison.

7. A cardiovascular system observation method which uses a computer processor for observing cardiovascular conditions of a patient based on pulse wave amplitude data, said data including information about pulse wave amplitude values and pulse wave intervals, and said data being obtained from pressure fluctuations which result from pulse waves which are issued from a body surface of said patient in a compressed state which changes between a higher pressure than a mean blood pressure of said patient and a lower pressure than said mean blood pressure, and based on blood pressure data showing one or more blood pressure values of said patient, said blood pressure data being calculated based on said pulse wave amplitude data, said cardiovascular system observation method comprising:

forming measurement patterns expressing transitions of said pulse wave amplitude values while pressure is gradually decreased or increased in said compressed state based on said pulse wave amplitude data;

extracting features of said measurement patterns by reference to a plurality of reference pattern groups corresponding to a plurality of cardiovascular conditions based on dynamic properties of blood vessels, cardiac output properties and blood pressure; and judging said measurement patterns to determine one or more of said reference pattern groups to which said measurement patterns belong by using said features obtained by said process steps for extracting features of said measurement patterns and said blood pressure data.

8. A cardiovascular system observation method as claimed in claim 7, wherein in said forming measurement patterns, an envelope for expressing transitions of said pulse wave amplitude values is obtained by securing a curve adaptable to said pulse wave amplitude data.

9. A cardiovascular system observation method as claimed in claim 7 and further comprising:

displaying information about said measurement patterns on a display screen of a displaying means, said information including shapes of said measurement patterns which is obtained by figuring or graphing said pulse wave amplitude data or said measurement patterns and also including one or more of said reference pattern groups to which said measurement patterns belong.

10. A cardiovascular system observation method as claimed in claim 9, wherein in said displaying information about said measurement patterns, said blood pressure values are displayed simultaneously on said display screen.

11. A cardiovascular system observation method as claimed in claim 9, wherein in said displaying information about said measurement patterns, a graphic portion corresponding to said pulse wave amplitude data is accumulatively displayed by calculating or graphing said pulse wave amplitude data.

12. A cardiovascular system observation method as claimed in claim 9 and further comprising:

recording one or more sets of information in conjunction with said measurement patterns and also in conjunction with said one or more reference pattern groups to which said measurement patterns belong; and retrieving said one or more sets of information and for displaying said set on said display screen of said displaying means.

13. A cardiovascular system observation method as claimed in claim 12, wherein in said recording said sets of information said blood pressure data is recorded together with said sets of information, and in said displaying information about said measurement patterns said blood pressure data and said sets of information are also displayed.

14. A product having a computer readable medium with computer logic recorded thereon for observing the cardiovascular conditions of a patient based on pulse wave amplitude data, said data including pulse wave amplitude values and pulse wave intervals which are obtained from pressure fluctuations resulting from pulse waves which are issued from a body surface of said patient in a compressed state which changes between a higher pressure than a mean blood pressure of said patient and a lower pressure than said mean blood pressure, said product comprising:

measurement pattern forming means for forming measurement patterns which express transitions of said pulse wave amplitude values while pressure is gradually decreased or increased in said compressed state based on said pulse wave amplitude data;

feature extracting means for extracting features of said measurement patterns by reference to a plurality of reference pattern groups corresponding to a plurality of cardiovascular conditions based on dynamic properties of blood vessels and cardiac properties; and pattern shape judging means for determining one or more of said reference pattern groups to which said measurement patterns belong by using said features obtained by said feature extracting means.

15. A product as claimed in claim 14, wherein said measurement pattern forming means obtains an envelope which expresses transitions of said pulse wave amplitude values by securing a curve adaptable to said pulse wave amplitude data.

16. A product as claimed in claim 14, wherein said feature extracting means extracts irregularities of said pulse wave intervals and features which express peak shapes in shapes of said measurement patterns, and said pattern shape judging means compares said irregularities of said pulse wave intervals and said features extracted by said feature extracting means with a plurality of parameters established in advance based on said plurality of reference pattern groups, and determines based on said comparison one or more of said reference pattern groups to which said measurement patterns belong.

17. A product as claimed in claim 14 and further comprising:

pattern displaying means for displaying information about said measurement patterns on a display screen of a displaying means connected to said computer, said information including shapes of said measurement patterns by calculating or graphing said pulse wave amplitude data or said measurement patterns and also including indications of one or more of said reference pattern groups to which said measurement patterns belong.

18. A product as claimed in claim 14 and further comprising:

information recording means for recording one or more sets of information in conjunction with said measurement patterns and also in conjunction with said one or more reference pattern groups to which said measurement patterns belong; and information displaying means which displays one or more recorded sets of information on a display screen of a displaying means connected to said computer.

* * * * *